United States Patent [19]

Camble et al.

[11] Patent Number: 5,068,222

[45] Date of Patent: Nov. 26, 1991

[54] BOMBESIN ANTAGONISTS WITH DELETION OF NET-RESIDUE AT THE C-TERMINUS

[75] Inventors: Roger Camble, Macclesfield; Ronald Cotton, Congleton; Anand S. Dutta, Stockport; Christopher F. Hayward, Macclesfield, all of England

[73] Assignee: Imperial Chemical Industries PLC, London, England

[21] Appl. No.: 265,566

[22] Filed: Nov. 1, 1988

[30] Foreign Application Priority Data

Nov. 2, 1987 [GB] United Kingdom ............. 8725598
Feb. 15, 1988 [GB] United Kingdom ............. 8803478
Jun. 6, 1988 [GB] United Kingdom ............. 8813355

[51] Int. Cl.$^5$ .................. A61K 37/02; C07K 7/06
[52] U.S. Cl. .................................... 514/15; 514/16; 530/326; 530/327; 530/328
[58] Field of Search ............... 530/326, 327, 328; 514/15, 16

[56] References Cited

U.S. PATENT DOCUMENTS

| | | |
|---|---|---|
| 4,332,661 | 6/1982 | Ford et al. |
| 4,405,778 | 9/1983 | Scartazzini et al. ............. 544/16 |
| 4,839,344 | 6/1989 | Bowers et al. |
| 4,866,160 | 9/1989 | Coy . |
| 4,943,561 | 7/1990 | Heimbrook et al. ............. 514/17 |

FOREIGN PATENT DOCUMENTS

| | | |
|---|---|---|
| 211267 | 2/1987 | European Pat. Off. |
| 315362 | 5/1987 | European Pat. Off. |
| 0339193 | 2/1989 | European Pat. Off. |
| 309297 | 3/1989 | European Pat. Off. |
| 0313158 | 4/1989 | European Pat. Off. |
| 402852 | 12/1990 | European Pat. Off. |
| 9003980 | 4/1990 | PCT Int'l Appl. |

8302272 7/1983 World Int. Prop. O. .

OTHER PUBLICATIONS

Heimbrook et al., Minimal Ligand Analysis of Gastrin Releasing Peptide, 1988, pp. 7016–7019.
Coy et al., Probing Peptide Backbone Function in Bombesin, 1988, pp. 5056–5060.
Bioactivities, vol. 2, No. 1, Mar. 1988, "Highly Specific Bombesin Rerceptor Antagonist", See also Other New Products from Bachem (Ibid).

Primary Examiner—Lester L. Lee
Assistant Examiner—Avis Davenport
Attorney, Agent, or Firm—Cushman, Darby & Cushman

[57] ABSTRACT

The invention relates to a polypeptide of formula I:

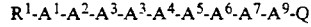

$$R^1\text{-}A^1\text{-}A^2\text{-}A^3\text{-}A^3\text{-}A^4\text{-}A^5\text{-}A^6\text{-}A^7\text{-}A^9\text{-}Q$$

wherein each of the generic terms is disclosed in full in the specification and includes: $R^1$ is (2-6C)alkanoyl or (1-4C)alkoxycarbonyl; $A^1$ is a direct link to $A^2$, or is Gly or Arg; $A^2$ is a direct link to $A^3$, or is Gly or Pro; $A^3$ is a direct link to $A^4$, or is Lys or Lys(Z); $A^4$ is His or D-His; $A^5$ is Trp or MeTrp; $A^6$ is Ala or MeAla; $A^7$ is Val or MeVal; $A^8$ is Gly or Sar; $A^9$ is His or MeHis; and Q is a group of the formula -$A^{10}.R^2$ in which $A^{10}$ is Leu or D-Leu and $R^2$ is hydroxy, amino, (1-3C)alkylamino or (1-3C)alkoxy; or Q is (1-6C)alkoxy or (1-10C)alkylamino; provided that when $R^1$ is acetyl and -$A^4$-$A^5$-$A^6$-$A^7$-$A^8$-$A^9$-Q is -His-Trp-Ala-Val-Gly-His-Leu-NH$_2$ then -$A^1$-$A^2$-$A^3$- is not a direct link to His.

The compounds possess antagonist properties against bombesin-like peptides and are of value in the treatment of malignant disease in warm-blooded animals.

9 Claims, No Drawings

BOMBESIN ANTAGONISTS WITH DELETION OF MET-RESIDUE AT THE C-TERMINUS

This invention relates to polypeptide compounds which possess antagonist properties against bombesin or bombesin-like peptides, hereinafter referred to as bombesin antagonist properties, and are of value, for example in the treatment of malignant disease in warm-blooded animals such as man. The invention includes novel polypeptide compounds and processes for their manufacture; novel pharmaceutical compositions containing said polypeptide compounds and processes for the manufacture of medicaments containing them for use in producing a bombesin antagonist effect in warm-blooded animals such as man.

Bombesin is a tetradecapeptide amide which was first isolated from the skin of the frog Bombina bombina (Anastasi, Erspamer and Bucci, *Experientia*, 1971, 27, 166). It is known that bombesin is a potent mitogen for mouse Swiss 3T3 fibroblast cells (Rozengurt and Sinnett-Smith, *Proc. Natl. Acad. Sci. U.S.A.*, 1983, 80, 2936) and that it stimulates amylase secretion from guinea pig pancreatic acini (Jensen, Jones, Folkers and Gardner, *Nature*, 1984, 309, 61). It is also known that bombesin-like peptides are produced and secreted by human small-cell lung cancer (SCLC) cells (Moody, Pert, Gazdar, Carney and Minna, *Science*, 1981, 214, 1246), that exogenously added bombesin-like peptides can stimulate the growth of human SCLC cells in vitro (Carney, Cuttita, Moody and Minna, *Cancer Research*, 1987, 47, 821) and that a monoclonal antibody specific for the C-terminus region of bombesin can prevent the growth of human SCLC cells both in vitro and in vivo (Cuttita, Carney, Mulshine, Moody, Fedorko, Fischler and Minna, *Nature*, 1985, 316, 823).

Gastrin releasing peptide (GRP) is a 27 amino-acid peptide amide isolated from the porcine gut (McDonald, Jornvall, Nilsson, Vagne, Ghatei, Bloom and Mutt, *Biochem. Biophys. Res. Commun.*, 1979, 90, 227) in which the C-terminus amino acid sequence is almost identical to that of bombesin. Neuromedin C (or GRP (18-27)) is a decapeptide amide, the structure of which is identical to the last ten amino acids in the C-terminus region of GRP, which has been isolated from the canine small intestine (Reeve, Walsh, Chew, Clark, Hawke and Shively, *J. Biol. Chem.*, 1983, 258, 5582). Both GRP and Neuromedin C possess bombesin-like properties (Zachary and Rogengurt, *Proc. Natl. Acad. Sci. U.S.A.*, 1985, 82, 7616). The structures of bombesin and Neuromedin C are shown below:

Bombesin:
Glp-Gln-Arg-Leu-Gly-Asn-Gln-Trp-Ala-Val-Gly-His-Leu-Met-NH$_2$

Neuromedin C:
H-Gly-Asn-His-Trp-Ala-Val-Gly-His-Leu-Met-NH$_2$

Several bombesin antagonists are known whereby the structure of the undecapeptide, substance P, is modified by the replacement of several of its L-amino acids with D-amino acids (Jensen, Jones, Folkers and Gardner, *Nature*, 1984, 309, 61; Zachary and Rozengurt, *Proc. Natl. Acad. Sci. U.S.A.*, 1985, 82, 7616 and Heinz-Erian, Folkers, Gardner and Jensen, *Gastroenterology*, 1986, 90, 1455). A few bombesin antagonists derived from the structure of bombesin have also been disclosed: thus [D-Glp$^7$, D-Ala$^{11}$, Ala$^{14}$]bombesin (7-14) was stated to be a partial antagonist of bombesin-induced hypothermia in the rat (Markl, Brown and Rivier, *Peptides*, 1981, 2, Suppl. 2, 169) and [D-Phe$^{12}$]bombesin, [D-Phe$^{12}$, Leu$^{14}$]bombesin and [Tyr$^4$, D-Phe$^{12}$]bombesin inhibited bombesin-stimulated secretion of amylase from guinea pig pancreatic acini (Heinz-Erian, Coy, Tamura, Jones, Gardner and Jensen, *Amer. J. Physiol.*, 1987, 252, G439).

In addition it has been disclosed that [Leu$^{13}$-$\psi$(CH$_2$-NH)-Leu$^{14}$]bombesin and [Ala$^9$-$\psi$(CH$_2$-NH)-Val$^{10}$, Leu$^{14}$]bombesin are bombesin antagonists (Coy, Heinz-Erian, Jiang and Jensen, *Regulatory Peptides*, 1987, 19, 105; International Symposium on Bombesin-like Peptides, Rome, October, 1987; Coy et al., *J. Biol. Chem.*, 1988, 263, 5056).

It has now been discovered that certain Neuromedin C derivatives are potent bombesin antagonists and this is a basis for the invention.

According to the invention there is provided a polypeptide of formula I:

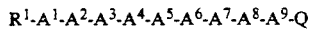
$$R^1\text{-}A^1\text{-}A^2\text{-}A^3\text{-}A^4\text{-}A^5\text{-}A^6\text{-}A^7\text{-}A^8\text{-}A^9\text{-}Q \qquad \text{I}$$

wherein
$R^1$ is hydrogen or (1-6C)alkyl which may optionally bear a phenyl substituent, and wherein said phenyl substituent may optionally bear a substituent selected from halogeno, (1-4C)alkyl, (1-4C)alkoxy, hydroxy, cyano and nitro, or $R^1$ is (2-6C)alkanoyl which may optionally bear one or more substituents selected from carboxy, (1-4C)alkoxycarbonyl, amino, (1-4C)alkylamino, di[(1-4C)alkyl]amino, phenyl, phenoxy, naphthyl, imidazolyl, naphthyloxy, pyridyl, indolyl and thienyl, and wherein any one or more of said aryl, phenoxy, naphthyloxy or heteroaryl groups may optionally bear one or more substituents selected from halogeno, (1-4C)alkyl, (1-4C)alkoxy, hydroxy, cyano and nitro; or
$R^1$ is (4-6C)cycloalkoxycarbonyl; or $R^1$ is (1-4C)alkoxycarbonyl which may optionally bear one or two phenyl substituents and wherein either one or both of said phenyl substituents may optionally bear a halogeno, nitro or (1-4C)alkoxy substituent;
wherein $A^1$ is a direct link to $A^2$, or is Gly, Arg, D-Arg, Lys, Lys(Z), Phe, D-Phe, Asp, L-Nal, D-Nal, D-pcF, D-pbF, D-pfF, D-dcF, Pro, D-Deh, $\beta$Ala or Glp;
wherein $A^2$ is a direct link to $A^3$, or is Gly, Pro or Asn;
wherein $A^3$ is a direct link to $A^4$, or is Lys, Lys(Z), D-Nal or D-pcF;
wherein $A^4$ is His, D-His, MeHis, EtHis, PrHis, His($\tau$-Me), His($\pi$-Me), D-Gln, D-Glu(OMe), D-Glp, Leu, D-Leu, MeLeu, Lys, Pal, D-Pal, Phe, D-Phe, Pro, Arg, Glu, His(COPh), Trp or Thr;
wherein $A^5$ is Trp, MeTrp, Trp(Me), Trp(For), Val, DL-Flg, L-Nal, pcF, Leu, Lys, Pal, Cha, Lys(Z(2Cl)) or Lys(COCH$_3$);
wherein $A^6$ is Ala, MeAla, Aib, Gly, Pro, Leu, Phe, D-Phe, Ser, Val, L-Nal, Thr, Arg or Glu;
wherein $A^7$ is Val, MeVal, Aib, Leu, Ile, Thr(CH$_2$Ph), Thr, Phe, D-Phe, Lys(Z(2Cl)), Ser or DL-Flg;
wherein $A^8$ is Gly, Sar, Ala, D-Ala, D-Ser, D-Ser(CH$_2$Ph), D-pcF, D-Ala(NH$_2$), D-Ala(NHZ(Cl)), Aib, D-Pro, D-Lys, Asp, D-Arg, D-Lys(Z(2Cl)), Val, Ac³c, Ac⁵c or Ac⁶c;

wherein $A^9$ is His, MeHis, His($\tau$-Me), His($\pi$-Me), D-pcF, Aib, Val, Leu, MeLeu, Ala, Ile, Ahx, Ape, Met, Pro, Phe, D-Phe, Gln, Lys, Lys(Z), Pal, Ser, Ser(CH₂Ph), Thr, Thr(CH₂Ph), Glu, Asp, Asp(OBuᵗ), Trp or L-Nal; and wherein Q is a group of the formula -$A^{10}$.$R^2$ in which $A^{10}$ is Leu, D-Leu, MeLeu, Ile, MeIle, Ahx, MeAhx, Aib, Pro, Val, MeVal, Phe, Ape, MeApe, Met, Ser, Gln, Glu or Trp and $R^2$ is hydroxy or amino; or $R^2$ is (1-3C)alkylamino, dialkylamino of up to 4 carbon atoms, or (1-3C)alkoxy, each optionally bearing a hydroxy, (1-3C)alkoxy, amino, (1-6C)alkylamino, dialkylamino of up to 8 carbon atoms, or phenyl-(1-3C)alkylamino substituent, other than in a position alpha to an oxygen or nitrogen atom, or a fluoro-(1-3C)alkyl or phenyl substituent; or $R^2$ is (3-6C)cycloalkylamino, N-alkyl-N-cycloalkylamino of up to 8 carbon atoms, or dicycloalkylamino of up to 12 carbon atoms; or $R^2$ is 1-pyrrolidinyl, piperidino, morpholino, 1-piperazinyl or 4-methylpiperazin-1-yl; or Q is (1-6C)alkoxy, (1-10C)alkylamino or dialkylamino of up to 10 carbon atoms each optionally bearing a hydroxy, amino, (1-3C)alkoxy, (1-6C)alkylamino, dialkylamino of up to 8 carbon atoms, phenyl-(1-3C)alkylamino substituent, other than in a position alpha to an oxygen or nitrogen atom, or a phenyl substituent; or Q is phenyl-(1-3C)alkylamino; or Q is (3-6C)cycloalkylamino, N-alkyl-N-cycloalkylamino of up to 8 carbon atoms or dicycloalkylamino of up to 12 carbon atoms; or Q is 1-azetidinyl, 1-pyrrolidinyl, piperidino, morpholino, 1-piperazinyl or 1-homopiperidinyl each optionally bearing on any available position, including on any available nitrogen atom, a substituent selected from (1-6C)alkyl, phenyl and phenyl-(1-3C)alkyl; and wherein within $R^2$ or Q a phenyl group may optionally bear a substituent selected from halogeno, (1-4C)alkyl, (1-4C)alkoxy, hydroxy and cyano;

or a pharmaceutically-acceptable salt of said polypeptide; provided that when $R^1$ is acetyl and -$A^4$-$A^5$-$A^6$-$A^7$-$A^8$-$A^9$-Q is -His-Trp-Ala-Val-Gly-His-Leu-NH₂ then -$A^1$-$A^2$-$A^3$- is not a direct link to His.

In this specification the term "alkyl" includes both straight and branched alkyl groups but references to individual alkyl groups such as "propyl" are specific for the straight chain version only. An analogous convention applies to other generic terms.

In the above formula I and throughout this specification, the amino acid residues are designated by their standard abbreviations (*Pure and Applied Chemistry*, 1974, 40, 317-331; *European Journal of Biochemistry*, 1984, 138, 9-37).

For the avoidance of doubt it is stated that:
amino acid symbols denote the L-configuration unless otherwise indicated by D or DL appearing before the symbol and separated from it by a hyphen;

Glp designates pyroglutamic acid, i.e. 5-oxopyrrolidine-2-carboxylic acid;

Nal designates 3-(2-naphthyl)alanine, i.e. 2-amino-3-(2-naphthyl)propanoic acid;

pcF designates 4-chlorophenylalanine, i.e. 2-amino-3-(4-chlorophenyl)propanoic acid;

pbF designates 4-bromophenylalanine;

pfF designates 4-fluorophenylalanine;

dcF designates 3,4-dichlorophenylalanine;

Deh designates (2,3-diethylguanidino)homoarginine, i.e. 2-amino-6-(2,3-diethylguanidino)hexanoic acid;

Pal designates 3-(3-pyridyl)alanine i.e. 2-amino-3-(3-pyridyl)propanoic acid;

Flg designates 2-(9-fluorenyl)glycine i.e. 2-amino-2-(9-fluorenyl)acetic acid;

Cha designates 3-cyclohexylalanine i.e. 2-amino-3-cyclohexylpropanoic acid;

Lys(Z(2Cl)) designates $N^6$-(2-chlorobenzyloxycarbonyl)lysine i.e. 2-amino-6-(2-chlorobenzyloxycarbonylamino)hexanoic acid;

Lys(COCH₃) designates $N^6$-acetyllysine i.e. 2-amino-6-acetamidohexanoic acid;

Aib designates 2-aminoisobutyric acid i.e. 2-amino-2-methylpropanoic acid;

Sar designates sarcosine i.e. N-methylglycine;

Thr(CH₂Ph) designates $O^3$-benzylthreonine i.e. 2-amino-3-benzyloxybutanoic acid;

Ser(CH₂Ph) designates $O^3$-benzylserine i.e. 2-amino-3-benzyloxypropanoic acid;

Ala(NH₂) designates 3-aminoalanine, i.e. 2,3-diaminopropanoic acid;

Ala(NHZ(Cl)) designates 3-(4-chlorobenzyloxycarbonylamino)alanine i.e. 2-amino-3-(4-chlorobenzyloxycarbonylamino)propanoic acid;

Ac³c designates 1-amino-1-cyclopropanecarboxylic acid;

Ac⁵c designates 1-amino-1-cyclopentanecarboxylic acid;

Ac⁶c designates 1-amino-1-cyclohexanecarboxylic acid;

Ahx designates (2S)-2-aminohexanoic acid, i.e. norleucine; and

Ape designates (2S)-2-aminopentanoic acid, i.e. norvaline.

Suitable values for the generic radicals referred to above include those set out below.

A suitable value for $R^1$ or a substituent on Q when it is (1-6C)alkyl is, for example, methyl, ethyl, propyl, isopropyl, butyl, isobutyl, pentyl or hexyl.

A suitable value for $R^1$ when it is (2-6C)alkanoyl is, for example, acetyl, propionyl, butyryl, isobutyryl, valeryl, isovaleryl, pivaloyl or hexanoyl.

A suitable value for $R^1$ when it is (1-4C)alkoxycarbonyl or for a (1-4C)alkoxycarbonyl substituent which may be present on $R^1$ is, for example, methoxycarbonyl, ethoxycarbonyl, propoxycarbonyl, isopropoxycarbonyl or tert-butoxycarbonyl.

A suitable value for a (1-4C)alkylamino or di-[(1-4C)alkyl]amino substituent on $R^1$ is, for example, methylamino, dimethylamino, ethylamino, diethylamino, propylamino, dipropylamino, isopropylamino or butylamino.

Suitable values for substituents which may be present on a phenyl, phenoxy, naphthyl, naphthyloxy, imidazolyl, pyridyl, indolyl or thienyl substituent on $R^1$ include the following, for example:

for halogeno: fluoro, chloro, bromo and iodo;

for (1-4C)alkyl: methyl, ethyl, propyl, isopropyl and butyl;

for (1-4C)alkoxy: methoxy, ethoxy, propoxy, isopropoxy and butoxy.

A suitable value for the number of substituents whch may be present on $R^1$ when it is (2-6C)alkanoyl, or on an aryl, phenoxy, naphthyloxy or heteroaryl substituent on $R^1$ is, for example, one, two or three.

A suitable value for $R^1$ when it is (4–6C)cycloalkoxycarbonyl is, for example, cyclobutoxycarbonyl, cyclopentyloxycarbonyl or cyclohexyloxycarbonyl.

A suitable value for $R^2$ when it is (1–3C)alkylamino or dialkylamino of up to 4 carbon atoms is, for example, methylamino, dimethylamino, ethylamino, N-ethyl-N-methylamino, propylamino, isopropylamino or diethylamino.

A suitable value for $R^2$, a substituent on $R^2$, or a substituent on Q when it is (1–3C)alkoxy is, for example, methoxy, ethoxy, propoxy or isopropoxy.

A suitable value for a substituent on $R^2$ or for a substituent on Q when it is (1–6C)alkylamino, dialkylamino of up to 8 carbon atoms, fluoro-(1–3C)alkyl or phenyl-(1–3C)alkylamino is, for example, methylamino, ethylamino, propylamino, isopropylamino, butylamino, isobutylamino, sec-butylamino, tert-butylamino, pentylamino, isopentylamino, hexylamino, isohexylamino, 3-methylpentylamino, dimethylamino, diethylamino, dipropylamino, N-ethyl-N-methylamino, N-methyl-N-propylamino, N-butyl-N-methylamino, N-methyl-N-pentylamino, N-isopentyl-N-methylamino, N-hexyl-N-methylamino, fluoromethyl, difluoromethyl, trifluoromethyl, 2,2,2-trifluoroethyl, 3,3,3-trifluoropropyl, benzylamino, phenethylamino or 3-phenylpropylamino.

A suitable value for Q when it is (1–6C)alkoxy is, for example, methoxy, ethoxy, propoxy, isopropoxy, butoxy, isobutoxy, sec-butoxy, tert-butoxy, pentyloxy or isopentyloxy.

A suitable value for Q when it is (1–10C)alkylamino or dialkylamino of up to 10 carbon atoms is, for example, methylamino, ethylamino, propylamino, isopropylamino, butylamino, isobutylamino, sec-butylamino, tert-butylamino, pentylamino, isopentylamino, hexylamino, isohexylamino, 3-methylpentylamino, 1-ethylpropylamino, 1-ethylpentylamino, 1,3-dimethylbutylamino, 1-ethyl-3-methylbutylamino, 1,4-dimethylpentylamino, 1-ethyl-4-methylpentylamino, dimethylamino, diethylamino, dipropylamino, N-ethyl-N-methylamino, N-methyl-N-propylamino, N-butyl-N-methylamino, N-methyl-N-pentylamino, N-isopentyl-N-methylamino or N-hexyl-N-methylamino.

A suitable value for Q when it is (1–6C)alkylamino or dialkylamino of up to 8 carbon atoms is, for example, methylamino, ethylamino, propylamino, isopropylamino, butylamino, isobutylamino, sec-butylamino, tert-butylamino, pentylamino, isopentylamino, hexylamino, isohexylamino, 3-methylpentylamino, 1-ethylpropylamino, 1,3-dimethylbutylamino, dimethylamino, diethylamino, dipropylamino, N-ethyl-N-methylamino, N-methyl-N-propylamino, N-butyl-N-methylamino, N-methyl-N-pentylamino or N-isopentyl-N-methylamino.

A suitable value for Q when it is phenyl-(1–3C)alkylamino is, for example, benzylamino, phenethylamino or 3-phenylpropylamino.

A suitable value for a phenyl-(1–3C)alkyl substituent on Q is, for example, benzyl, phenethyl or 3-phenylpropyl.

Suitable values for substituents which may be present on a phenyl or phenyl-(1–3C)alkylamino substituent on $R^2$, on a phenyl-(1–3C)-alkylamino, phenyl or phenyl-(1–3C)alkyl substituent on Q, or on the phenyl group when Q is phenyl-(1–3C)alkylamino, include the following, for example:

for halogeno: fluoro, chloro, bromo and iodo;

for (1–4C)alkyl: methyl, ethyl, propyl, isopropyl and butyl;

for (1–4C)alkoxy: methoxy, ethoxy, propoxy, isopropoxy and butoxy.

A suitable value for $R^2$ or for Q when it is (3–6C)cycloalkylamino, N-alkyl-N-cycloalkylamino of up to 8 carbon atoms or dicycloalkylamino of up to 12 carbon atoms is, for example, cyclopropylamino, cyclobutylamino, cyclopentylamino, cyclohexylamino, N-cyclopentyl-N-methylamino, N-cyclohexyl-N-methylamino, dicylopentylamino or dicyclohexylamino.

A suitable pharmaceutically-acceptable salt of the invention may be for those polypeptide compounds of the invention which are sufficiently basic (for example those which contain an Arg, D-Arg, Lys, D-Lys, D-Deh, His, D-His, MeHis, EtHis, PrHis, D-Ala(NH$_2$), His($\tau$-Me) or His($\pi$-Me) group or those where the N-terminus is not acylated) an acid-addition salt and for those polypeptide compounds of the invention which are sufficiently acidic (for example those which contain a carboxy substituent or wherein $R^2$ is hydroxy) a base-addition salt.

A suitable pharmaceutically-acceptable acid-addition salt of the invention may be formed with an inorganic acid, for example hydrochloric acid, hydrobromic acid, sulphuric acid or phosphoric acid, or with an organic acid, for example acetic acid, citric acid, maleic acid, fumaric acid, succinic acid, tartaric acid or trifluoroacetic acid.

Suitable pharmaceutically-acceptable base-addition salts of the invention include, for example, alkali metal (such as sodium or potassium), alkaline earth metal (such as calcium or magnesium), and ammonium salts, and salts with organic bases, for example salts with methylamine, dimethylamine and trimethylamine.

A particular group of compounds of the invention comprises polypeptide compounds of the formula I wherein $R^1$ is hydrogen, methyl, ethyl, propyl, isopropyl, benzyl, acetyl, propionyl, butyryl, isobutyryl, isovaleryl, benzyloxycarbonyl, phenylacetyl, 3-phenylpropionyl, 4-chlorophenylacetyl, 3-chlorophenylacetyl, 4-bromophenylacetyl, 4-fluorophenylacetyl, naphthylacetyl, imidazolylacetyl, pyridylacetyl, thienylacetyl, indolylacetyl, phenoxyacetyl, naphthyloxyacetyl, 3-carboxypropionyl, 3-methoxycarbonylpropionyl, glycyl, 3-aminopropionyl, tert-butoxycarbonyl or cyclopentyloxycarbonyl; wherein $A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

wherein $A^2$ is a direct link to $A^3$, or is Gly, Pro or Asn;

wherein $A^3$ is a direct link to $A^4$, or is Lys, Lys(Z), D-Nal or D-pcF;

wherein $A^4$ is His, D-His, MeHis, EtHis, PrHis, His($\tau$-Me), His($\pi$-Me), D-Gln, Lys, Pal, D-Pal, Phe, Pro, D-Glu(OMe), D-Glp or Trp;

wherein $A^5$ is Trp, MeTrp, Trp(Me), Trp(For), L-Nal, pcF, Lys or Pal;

wherein $A^6$ is Ala, MeAla, Aib, Gly, Leu, Ser, Val or Thr;

wherein $A^7$ is Val, MeVal, Aib, Leu, Ile or Thr;

wherein $A^8$ is Gly, Sar, D-Ala, D-Ser, D-Ser(CH$_2$Ph), D-pcF, Aib or D-Pro;

wherein $A^9$ is His, MeHis, His($\tau$-Me), His($\pi$-Me), Val, Leu, Pro, Phe, Gln, Lys, Lys(Z) or Pal; and wherein Q is a group of the formula -A$^{10}$.R$^2$ in which A$^{10}$ is Leu, D-Leu, MeLeu, Ile, Ahx, Aib, Val, Phe, Ape or Met and R$^2$ is hydroxy or amino; or R$^2$ is (1–3C)alkylamino (especially methylamino and ethylamino), dialkylamino of up to 4 carbon atoms (especially dimethylamino and N-ethyl-N-methylamino) or (1–3C)alkoxy (especially methoxy and ethoxy), each optionally bearing an amino, (1–6C)alkylamino (especially methylamino, ethylamino, isobutylamino and isopentylamino) or phenyl-(1–3C)alkylamino (especially benzylamino and phenethylamino) substituent, other than in a position alpha to an oxygen or nitrogen atom, or a fluoro-(1–3C)alkyl (especially trifluoromethyl) or phenyl substituent; or R$^2$ is (3–6C)cycloalkylamino (especially cyclopentylamino and cyclohexylamino); or R$^2$ is 1-pyrrolidinyl, piperidino, morpholino or 1-piperazinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is (3–6C)cycloalkylamino (especially cyclopentylamino and cyclohexylamino);

or Q is 1-pyrrolidinyl, piperidino, morpholino or 1-piperazinyl, each optionally bearing on any available position, including on any available nitrogen atom, a substituent selected from (1–6C)alkyl (especially methyl and ethyl), phenyl and phenyl-(1–3C)alkyl (especially benzyl and phenethyl); and wherein within Q a phenyl group may optionally bear a substituent selected from chloro, methyl, methoxy and hydroxy; and the pharmaceutically-acceptable salts thereof;

provided that when R$^1$ is acetyl and -A$^4$-A$^5$-A$^6$-A$^7$-A$^8$-A$^9$-Q is -His-Trp-Ala-Val-Gly-His-Leu-NH$_2$ then -A$^1$-A$^2$-A$^3$- is not a direct link to His.

A preferred group of compounds of the invention comprises polypeptide compounds of the formula I wherein R$^1$ is hydrogen, methyl, ethyl, propyl, isopropyl, acetyl, propionyl, isobutyryl, isovaleryl, benzyloxycarbonyl, phenylacetyl, 3-phenylpropionyl, 4-chlorophenylacetyl, naphth-2-ylacetyl, 4-pyridylacetyl, indol-3-ylacetyl, naphth-2-yloxyacetyl, 3-carboxypropionyl or tert-butoxycarbonyl;

A$^1$ is a direct link to A$^2$, or is Gly, Arg, D-Arg, Lys, Lys(Z), Phe, D-Phe, Asp, D-pcF, D-Deh, L-Nal, βAla, D-Nal or Pro;

A$^2$ is a direct link to A$^3$, or is Gly, Pro or Asn;

A$^3$ is a direct link to A$^4$, or is Lys, Lys(Z), D-Nal or D-pcF;

A$^4$ is His, D-His, His(τ-Me), His(π-Me), D-Gln, Leu, Lys, Pal, D-Pal, Phe, Pro, D-Glu(OMe) or D-Glp; A$^5$ is Trp or MeTrp; A$^6$ is Ala, MeAla or Aib; A$^7$ is Val; A$^8$ is Gly, Sar, D-Ala, D-Ser, D-Ser(CH$_2$Ph), D-pcF, Aib or D-Pro; A$^9$ is His, MeHis, His(τ-Me), His(π-Me), Leu, Pro, Gln, Phe, Lys, Lys(Z) or Pal; and Q is a group of the formula -A$^{10}$.R$^2$ in which A$^{10}$ is Leu, MeLeu, Phe or Val and R$^2$ is methoxy, amino or methylamino, each optionally bearing a trifluoromethyl or phenyl substituent, or R$^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent;

or R$^2$ is cyclopentylamino or 1-pyrrolidinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is cyclopentylamino, cyclohexylamino, piperidino, 4-phenylpiperidino, morpholino or 4-benzylpiperazin-1-yl;

and the pharmaceutically-acceptable acid-addition salts thereof;

provided that when R$^1$ is acetyl and -A$^4$-A$^5$-A$^6$-A$^7$-A$^8$-A$^9$-Q is -His-Trp-Ala-Val-Gly-His-Leu-NH$_2$ then -A$^1$-A$^2$-A$^3$- is not a direct link to His.

A further particular group of compounds of the invention comprises polypeptide compounds of the formula I wherein R$^1$ is hydrogen, methyl, ethyl, propyl, isopropyl, benzyl, acetyl, propionyl, butyryl, benzyloxycarbonyl, phenylacetyl, 3-phenylpropionyl, 4-chlorophenylacetyl, 3-chlorophenylacetyl, 4-bromophenylacetyl, 4-fluorophenylacetyl, naphthylacetyl, imidazolylacetyl, pyridylacetyl, thienylacetyl, indolylacetyl, phenoxyacetyl, naphthyloxyacetyl, 3-carboxypropionyl, 3-methoxycarbonylpropionyl, glycyl, 3-aminopropionyl, tert-butoxycarbonyl or cyclopentyloxycarbonyl;

wherein A$^1$ is a direct link to A$^2$, or is Gly, Arg, D-Arg, Lys, Lys(Z), Phe, D-Phe, Asp, D-pcF, D-Deh, L-Nal, βAla, D-Nal or Pro;

wherein A$^2$ is a direct link to A$^3$, or is Gly, Pro or Asn;

wherein A$^3$ is a direct link to A$^4$, or is Lys, Lys(Z), D-Nal or D-pcF;

wherein A$^4$ is His, D-Gln, Lys, Pal, D-Glu(OMe) or D-Glp;

wherein A$^5$ is Trp, MeTrp, Trp(Me), Trp(For), L-Nal, pcF, Lys or Pal;

wherein A$^6$ is Ala, MeAla, Aib, Gly, Leu, Ser, Val or Thr;

wherein A$^7$ is Val, MeVal, Aib, Leu, Ile or Thr;

wherein A$^8$ is Gly, Sar, Ala, D-Ala, D-Ser, Aib, D-Pro or Phe;

wherein A$^9$ is His, MeHis, His(τ-Me), His(π-Me), Gln or Lys; and wherein Q is a group of the formula -A$^{10}$.R$^2$ in which A$^{10}$ is Leu, D-Leu, MeLeu, Ile, Ahx, Aib, Val, Ape or Met and R$^2$ is hydroxy or amino; or R$^2$ is (1–3C)alkylamino (especially methylamino and ethylamino), dialkylamino of up to 4 carbon atoms (especially dimethylamino and N-ethyl-N-methylamino) or (1–3C)alkoxy (especially methoxy and ethoxy), each optionally bearing an amino, (1–6C)alkylamino (especially methylamino, ethylamino, isobutylamino and isopentylamino) or phenyl-(1–3C)alkylamino (especially benzylamino and phenethylamino) substituent, other than in a position alpha to an oxygen or nitrogen atom, or a fluoro-(1–3C)alkyl (especially trifluoromethyl) or phenyl substituent; or R$^2$ is (3–6C)cycloalkylamino (especially cyclopentylamino and cyclohexylamino); or R$^2$ is 1-pyrrolidinyl, piperidino, morpholino or 1-piperazinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is (3-6C)cycloalkylamino (especially cyclopentylamino and cyclohexylamino);

or Q is 1-pyrrolidinyl, piperidino, morpholino or 1-piperazinyl, each optionally bearing on any available position, including on any available nitrogen atom, a substituent selected from (1-6C)alkyl (especially methyl and ethyl), phenyl and phenyl-(1-3C)alkyl (especially benzyl and phenethyl); and wherein within Q a phenyl group may optionally bear a substituent selected from chloro, methyl, methoxy and hydroxy; and the pharmaceutically-acceptable salts thereof;

provided that when $R^1$ is acetyl and $-A^4-A^5-A^6-A^8-A^9$-Q is -His-Trp-Ala-Val-Gly-His-Leu-NH$_2$ then $-A^1-A^2-A^3$- is not a direct link to His.

A further preferred group of compounds of the invention comprises polypeptide compounds of the formula I
wherein $R^1$ is hydrogen, methyl, ethyl, propyl, isopropyl, acetyl, propionyl, benzyloxycarbonyl, phenylacetyl, 3-phenylpropionyl, 4-chlorophenylacetyl, naphth-2-ylacetyl, indol-3-ylacetyl, naphth-2-yloxyacetyl, 3-carboxypropionyl or tert-butoxycarbonyl;

$A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

$A^2$ is a direct link to $A^3$, or is Gly, Pro or Asn;

$A^3$ is a direct link to $A^4$, or is Lys, Lys(Z), D-Nal or D-pcF;

$A^4$ is His, D-Gln, Lys, Pal, D-Glu(OMe) or D-Glp;
$A^5$ is Trp or MeTrp;

$A^6$ is Ala, MeAla or Aib; $A^7$ is Val; $A^8$ is Gly, Sar, D-Ala, Aib or D-Pro; $A^9$ is His, MeHis, His(τ-Me), His(π-Me), Gln or Lys; and Q is a group of the formula $-A^{10}.R^2$ in which $A^{10}$ is Leu or Val and $R^2$ is methoxy, amino or methylamino, each optionally bearing a trifluoromethyl or phenyl substituent, or $R^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent;

or $R^2$ is cyclopentylamino or 1-pyrrolidinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is cyclopentylamino, cylcohexylamino, piperidino, 4-phenylpiperidino, morpholino or 4-benzylpiperazin-1-yl;

and the pharmaceutically-acceptable acid-addition salts thereof; provided that when $R^1$ is acetyl and $-A^4$-$A^5$-$A^6$-$A^7$-$A^8$-$A^9$-Q is -His-Trp-Ala-Val-Gly-His-Leu-NH$_2$ then $-A^1$-$A^2$-$A^3$- is not a direct link to His.

An especially preferred group of compounds of the invention comprises polypeptide compounds of the formula I wherein $R^1$ is hydrogen, isopropyl, acetyl, propionyl, benzyloxycarbonyl, 3-phenylpropionyl, 4-chlorophenylacetyl, naphth-2-ylacetyl, indol-3-ylacetyl, naphth-2-yloxyacetyl, 3-carboxypropionyl or tert-butoxycarbonyl;

$A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

$A^2$ is a direct link to $A^3$, or is Gly, Pro or Asn;

$A^3$ is a direct link to $A^4$, or is Lys, Lys(Z), D-Nal or D-pcF;

$A^4$ is His, D-Gln or D-Glu(OMe);

$A^5$ is Trp; $A^6$ is Ala; $A^7$ is Val;

$A^8$ is Gly, Sar or D-Ala; $A^9$ is His; and

Q is a group of the formula $-A^{10}.R^2$ in which $A^{10}$ is Leu and $R^2$ is methoxy, amino, methylamino, ethylamino or dimethylamino; or Q is methoxy or isopentylamino;

and the pharmaceutically-acceptable salts thereof;

provided that when $R^1$ is acetyl and $-A^4$-$A^5$-$A^6$-$A^7$-$A^8$-$A^9$-Q is -His-Trp-Ala-Val-Gly-His-Leu-NH$_2$ then $-A^1$-$A^2$-$A^3$- is not a direct link to His.

A further preferred group of compounds of the invention comprises polypeptides of the formula I
wherein $R^1$ is hydrogen, acetyl, propionyl, butyryl, benzyloxycarbonyl, 3-phenylpropionyl, naphthylacetyl, tert-butoxycarbonyl or cyclopentyloxycarbonyl;

wherein $A^1$ is Gly, Arg, Lys(Z), Phe, D-Phe, D-pcF, D-Deh, L-Nal, D-Nal or Pro;

wherein $A^2$ is a direct link to $A^3$, or is Gly, Pro or Asn;

wherein $A^3$ is a direct link to $A^4$, or is Lys, Lys(Z), D-Nal or D-pcF;

wherein $A^4$ is His, D-His or D-Gln;

wherein $A^5$ is Trp; wherein $A^6$ is Ala; wherein $A^7$ is Val;

wherein $A^8$ is Gly or D-Ala; wherein $A^9$ is His;

and wherein Q is a group of the formula $-A^{10}.R^2$ in which $A^{10}$ is Leu and $R^2$ is hydroxy, amino, (1-3C)alkylamino (especially methylamino and ethylamino), dialkylamino of up to 4 carbon atoms (especially dimethylamino and N-ethyl-N-methylamino) or (1-3C)alkoxy (especially methoxy and ethoxy);

or Q is (1-6C)alkoxy (especially methoxy, isobutoxy and isopentyloxy), (1-6C)alkylamino (especially methylamino, isobutylamino and isopentylamino) or dialkylamino of up to 8 carbon atoms (especially dimethylamino, N-ethyl-N-methylamino and N-isopentyl-N-methylamino); and the pharmaceutically-acceptable salts thereof.

A further especially preferred group of compounds of the invention comprises polypeptides of the formula I
wherein $R^1$ is hydrogen, acetyl, benzyloxycarbonyl or tert-butoxycarbonyl;

$A^1$ is Gly, Arg, Lys(Z), D-pcF, D-Deh, D-Nal or Pro;

$A^2$ is a direct link to $A^3$, or is Gly, Pro or Asn;

$A^3$ is a direct link to $A^4$, or is Lys, Lys(Z), D-Nal or D-pcF;

$A^4$ is His or D-Gln; $A^5$ is Trp; $A^6$ is Ala; $A^7$ is Val; $A^8$ is Gly or D-Ala; $A^9$ is His; and Q is a group of the formula -A$^{10}$.R$^2$ in which A$^{10}$ is Leu and R$^2$ is methoxy, amino or methylamino;

or Q is isopentylamino;

and the pharmaceutically-acceptable acid-addition salts thereof.

A further preferred group of compounds of the invention comprises polypeptide compounds of the formula I
wherein R$^1$ is hydrogen, isopropyl, acetyl, propionyl, isobutyryl, isovaleryl, benzyloxycarbonyl, phenylacetyl, 3-phenylpropionyl, 4-chlorophenylacetyl, naphth-2-ylacetyl, 4-pyridylacetyl, indol-3-ylacetyl, naphth-2-yloxyacetyl, 3-carboxypropionyl or tert-butoxycarbonyl;

A$^1$ is a direct link to A$^2$, or is Gly, Arg, D-Arg, Lys, Lys(Z), Phe, D-Phe, Asp, D-pcF, D-Deh, L-Nal, βAla, D-Nal, Pro or Glp;

A$^2$ is a direct link to A$^3$, or is Gly, Pro or Asn;

A$^3$ is a direct link to A$^4$, or is Lys, Lys(Z), D-Nal or D-pcF;

A$^4$ is His, D-His, His(τ-Me), His(π-Me), D-Gln, Leu, MeLeu, Pal, D-Pal, Phe, Pro or D-Glu(OMe);

A$^5$ is Trp; A$^6$ is Ala or Ser; A$^7$ is Val or Ile;

A$^8$ is Gly, Sar, D-Ala, D-Ser, D-Ser(CH$_2$Ph), D-pcF, Aib or D-Pro;

A$^9$ is His, Val, Leu, Pro, Gln, Phe, Lys(Z), Pal, Ser, Ser(CH$_2$Ph), Thr, Thr(CH$_2$Ph), Trp or L-Nal; and Q is a group of the formula -A$^{10}$.R$^2$ in which A$^{10}$ is Leu, MeLeu, Ile, Val or Phe and R$^2$ is methoxy, methylamino or dimethylamino each optionally bearing a phenyl substituent, or R$^2$ is ethoxy, isopropoxy or ethylamino, each optionally bearing a hydroxy substituent, other than in a position alpha to an oxygen or nitrogen atom, or a phenyl substituent; or Q is isopentylamino or piperidino;

and the pharmaceutically-acceptable acid-addition salts thereof.

A further especially preferred group of compounds of the invention comprises polypeptide compounds of the formula I wherein R$^1$ is hydrogen, acetyl, propionyl, isobutyryl, isovaleryl, benzyloxycarbonyl, 3-phenylpropionyl, 4-chlorophenylacetyl, naphth-2-ylacetyl, indol-3-ylacetyl, naphth-2-yloxyacetyl, 3-carboxypropionyl or tert-butoxycarbonyl;

A$^1$ is a direct link to A$^2$, or is Gly, Arg, D-Arg, Lys(Z), Phe, D-Phe, D-pcF, D-Deh, L-Nal, βAla, D-Nal or Pro;

A$^2$ is a direct link to A$^3$, or is Pro or Asn;

A$^3$ is a direct link to A$^4$, or is Lys, Lys(Z), D-Nal or D-pcF;

A$^4$ is His, His(τ-Me), His(π-Me), D-Gln or MeLeu;

A$^5$ is Trp; A$^6$ is Ala or Ser; A$^7$ is Val or Ile;

A$^8$ is Gly, Sar, D-Ala or D-Pro; A$^9$ is His, Val, Leu, Phe, Lys(Z), Pal, Ser(CH$_2$Ph), Thr(CH$_2$Ph), Trp or L-Nal; and Q is a group of the formula -A$^{10}$.R$^2$ in which A$^{10}$ is Leu, MeLeu or Ile and R$^2$ is methoxy, methylamino, ethylamino, dimethylamino or 2-hydroxyethylamino;

or Q is piperidino;

and the pharmaceutically-acceptable salts thereof.

A further preferred group of compounds of the invention comprises polypeptide compounds of the formula I
wherein R$^1$ is acetyl, propionyl, isobutyryl, isovaleryl, benzyloxycarbonyl, 3-phenylpropionyl, 4-chlorophenylacetyl, indol-3-ylacetyl, 3-carboxypropionyl or tert-butoxycarbonyl;

A$^1$ is a direct link to A$^2$, or is Arg, Phe, Asp, D-Deh or βAla;

A$^2$ is a direct link to A$^3$, or is Pro;

A$^3$ is a direct link to A$^4$, or is Lys(Z);

A$^4$ is His, His(τ-Me), His(π-Me), D-Gln or Pro; A$^5$ is Trp; A$^6$ is Ala or Ser; A$^7$ is Val; A$^8$ is Gly, Sar or D-Ala;

A$^9$ is His, Gln or Lys(Z); and Q is a group of the formula -A$^{10}$.R$^2$ in which A$^{10}$ is Leu, MeLeu, Ile or Val and R$^2$ is methoxy or methylamino; and the pharmaceutically-acceptable salts thereof.

A further especially preferred group of compounds of the invention comprises polypeptide compounds of the formula I wherein R$^1$ is acetyl, propionyl, isobutyryl or benzyloxycarbonyl;

A$^1$ is a direct link to A$^2$;

A$^2$ is a direct link to A$^3$;

A$^3$ is a direct link to A$^4$;

A$^4$ is His;

A$^5$ is Trp; A$^6$ is Ala; A$^7$ is Val;

A$^8$ is or D-Ala; A$^9$ is His or Lys(Z); and

Q is a group of the formula -A$^{10}$.R$^2$ in which A$^{10}$ is Leu or MeLeu and R$^2$ is methoxy or methylamino and the pharmaceutically-acceptable salts thereof.

Specific preferred compounds of the invention include, for example, the following polypeptides of formula I:

1 Z-Arg-Pro-Lys(Z)-His-Trp-Ala-Val-Gly-His-Leu-OMe,
2 Z-Arg-Gly-Lys(Z)-His-Trp-Ala-Val-Gly-His-Leu-OMe,
3 Z-Arg-Pro-Lys(Z)-D-Gln-Trp-Ala-Val-D-Ala-His-Leu-OMe,
4 Boc-D-Deh-Pro-Lys(Z)-His-Trp-Ala-Val-D-Ala-His-Leu-OMe,
5 Ac-D-Deh-His-Trp-Ala-Val-D-Ala-His-Leu-OMe, and
6 Ac-D-Nal-His-Trp-Ala-Val-Gly-His-Leu-OMe;

and the pharmaceutically acceptable acid-addition salts thereof.

Further specific preferred compounds of the invention include, for example, the following polypeptides of formula I:

1. Ac-Phe-His-Trp-Ala-Val-D-Ala-His-Leu-OMe,
2. Ac-His-Trp-Ala-Val-D-Ala-His-Leu-OMe,
3. Indol-3-ylacetyl-His-Trp-Ala-Val-D-Ala-His-Leu-OMe,
4. Indol-3-ylacetyl-His-Trp-Ala-Val-D-Ala-His-Leu-NHMe,
5. Ac-His-Trp-Ala-Val-D-Ala-His-Leu-NHMe,
6. Propionyl-His-Trp-Ala-Val-D-Ala-His-Leu-OMe,
7. Ac-D-Gln-Trp-Ala-Val-D-Ala-His-Leu-OMe,
8. 3-Phenylpropionyl-His-Trp-Ala-Val-D-Ala-His-Leu-OMe and
9. Boc-βAla-His-Trp-Ala-Val-D-Ala-His-Leu-OMe;

and the pharmaceutically-acceptable acid-addition salts thereof.

Further specific preferred compounds of the invention include, for example, the following polypeptides of formula I:

1. Propionyl-His-Trp-Ala-Val-D-Ala-His-MeLeu-OMe,
2. Isovaleryl-His-Trp-Ala-Val-D-Ala-His-Leu-OMe, 3. Isobutyryl-His-Trp-Ala-Val-D-Ala-His-Leu-OMe,
4. Propionyl-His-Trp-Ala-Val-Sar-His-Leu-OMe,
5. Pivaloyl-His-Trp-Ala-Val-D-Ala-His-Leu-OMe and
6. Ac-Leu-Trp-Ala-Val-D-Ala-His-Leu-OMe;

and the pharmaceutically-acceptable acid-addition salts thereof.

Further specific preferred compounds of the invention, include, for example, the following polypeptides of formula I:
1. Ac-His-Trp-Ala-Val-D-Ala-His-Leu-NHMe,
2. Ac-His-Trp-Ala-Val-D-Ala-Lys(Z)-Leu-OMe,
3. Ac-Pro-Trp-Ala-Val-D-Ala-His-Leu-OMe,
4. Propionyl-His-Trp-Ala-Val-D-Ala-His-Leu-OMe,
5. Propionyl-His-Trp-Ala-Val-D-Ala-His-Leu-NHMe,
6. Propionyl-His-( -Me)-Trp-Ala-Val-D-Ala-His-Leu-OMe,
7. Propionyl-His-Trp-Ser-Val-D-Ala-His-Leu-OMe,
8. Propionyl-His-Trp-Ala-Val-D-Ala-His-MeLeu-OMe,
9. Propionyl-His-Trp-Ala-Val-D-Ala-His-MeLeu-NHMe,
10. Propionyl-His-Trp-Ala-Val-D-Ala-His-Ile-OMe,
11. Propionyl-His-Trp-Ala-Val-D-Ala-His-Val-OMe,
12. Isobutyryl-His-Trp-Ala-Val-D-Ala-His-Leu-OMe,
13. Isobutyryl-His-Trp-Ala-Val-D-Ala-His-Leu-NHMe,
14. Pivaloyl-His-Trp-Ala-Val-D-Ala-His-Leu-OMe,
15. Z-His-Trp-Ala-Val-D-Ala-His-Leu-OMe, and
16. Z-His-Trp-Ala-Val-D-Ala-His-MeLeu-OMe;

and the pharmaceutically-acceptable acid-addition salts thereof.

The polypeptide of the invention may be prepared by any process well known in the art of peptide chemistry to be applicable to the synthesis of analogous compounds. Thus, for example, a polypeptide of the invention may be obtained by procedures analogous to those disclosed in "Solid Phase Peptide Synthesis" by Stewart and Young (published by the Pierce Chemical Company, Illinois, 1984), "Principles of Peptide Synthesis" (published by Springer-Verlag, Berlin, 1984) and "Practice of Peptide Synthesis" (published by Springer-Verlag, Berlin, 1984).

Preferred processes for the manufacture of a polypeptide of the invention include, for example:

(a) the removal of one or more conventional peptide protecting groups from a protected polypeptide to give a polypeptide of the invention of formula I;

(b) the formation of an amide bond by coupling two peptide units, one containing a carboxylic acid group, or a reactive derivative thereof, and the other containing an amino group, such that a protected or unprotected polypeptide having the sequence indicated in formula I is produced whereafter, if necessary, the protecting groups are removed using process (a) above;

(c) for the manufacture of a polypeptide of the invention wherein $R^1$ is (2–6C)alkanoyl, which is unsubstituted or substituted as defined above, (4–6C)cycloalkoxycarbonyl or (1–4C)alkoxycarbonyl which is unsubstituted or substituted as defined above, the reaction of a protected or unprotected polypeptide having the sequence indicated in formula I wherein $R^1$ is hydrogen with a suitable acylating agent in the presence, if necessary, of a suitable base whereafter, if necessary, the protecting groups are removed using process (a) above;

(d) for the manufacture of a polypeptide of the invention wherein $R^2$ is (1–3C)alkoxy or Q is (1–6C)alkoxy, each optionally substituted as stated above, the esterification of a protected or unprotected polypeptide having the sequence indicated in formula I wherein $R^2$ or Q is hydroxy, or a reactive derivative thereof, with a suitable alcohol, whereafter, if necessary, the protecting groups are removed using process (a) above;

(e) for the manufacture of a polypeptide of the invention wherein $R^2$ is amino, (1–3C)alkylamino or dialkylamino of up to 4 carbon atoms, or Q is (1–10C)alkylamino, dialkylamino of up to 10 carbon atoms or phenyl-(1–3C)alkylamino each optionally substituted as stated above; or $R^2$ or Q is (3–6C)cycloalkylamino, N-alkyl-N-cycloalkylamino of up to 8 carbon atoms or dicycloalkylamino of up to 12 carbon atoms;

or $R^2$ is 1-pyrrolidinyl, piperidino, morpholino, 1-piperazinyl or 4-methylpiperazin-1-yl; or Q is 1-azirinyl, 1-azetidinyl, 1-pyrrolidinyl, piperidino, morpholino, 1-piperazinyl or 1-homopiperidinyl each optionally substituted as stated above, the reaction of a protected or unprotected polypeptide having the sequence indicated in formula I wherein $R^2$ or Q is hydroxy, or a reactive derivative thereof, or (1–6C)alkoxy, with ammonia, with a suitable alkylamine, dialkylamine or phenylalkylamine, with a suitable cycloalkylamine, N-alkyl-N-cycloalkylamine or dicycloalkylamine, or with the appropriate heterocycle whereafter, if necessary, the protecting groups are removed using process (a) above;

(f) for the manufacture of a polypeptide of the invention wherein $R^2$ is hydroxy, the hydrolysis of the protected or unprotected polypeptide having the sequence indicated in formula I wherein $R^2$ is (1–3C)alkoxy whereafter, if necessary, the protecting groups are removed using process (a) above; and (g) for the manufacture of a polypeptide of the invention wherein $R^1$ is (1–6C)alkyl which may optionally bear a phenyl substituent, the reaction of a protected or unprotected polypeptide having the sequence indicated in formula I wherein $R^1$ is hydrogen or wherein $R^1$ is hydrogen and wherein $R^2$, when Q is $-A^{10}.R^2$, or Q is a hydroxymethylated or a methylbenzhydrylamine cross-linked resin, with a suitable (1–6C)aldehyde or (3–6C)ketone, each optionally bearing a phenyl substituent, in the presence of a suitable reducing agent whereafter, if necessary, the polypeptide is released from the solid support and whereafter, if necessary, the protecting groups are removed using process (a) above.

In process (a) there may be as many protecting groups in the starting material as there are radicals which may require protection, for example some or all of those groups which exist in the product as free hydroxy groups or basic amino groups (whether primary or secondary amino groups). The protecting group or groups may be chosen from those described in the standard text books on peptide chemistry stated above. Various methods for the removal of the protecting group or groups are also described in those books.

In process (a) a suitable protecting group for a basic amino group (whether at the N-terminus or in an amino acid side chain) is, for example, an arylmethoxycarbonyl group, for example a Z-, $Z(NO_2)$-, $Z(Br)$-, $Z(Cl)$- or $Z(OMe)$- group, which may be removed by hydrogenation over a catalyst, for example palladium-on-charcoal or it may be removed by treatment with an inorganic acid, for example anhydrous hydrogen fluoride or hydrogen bromide.

In process (a) a particularly suitable protecting group for a basic amino group is, for example, an alkoxycarbonyl group, for example a Boc-group, which may be removed by treatment with an organic acid, for example trifluoroacetic acid, or it may be removed by treatment with an inorganic acid, for example anhydrous hydrogen chloride or hydrogen bromide; or for example a 9-fluorenylmethoxycarbonyl group, which may be removed by treatment with an organic base, for example piperidine.

In process (a) a particularly suitable protecting group for the basic amino group in the side chain of histidine is, for example, an arylsulphonyl group, for example a tosyl group, which may be removed by treatment with a hydroxylamine, for example an N-hydroxytriazole, particularly 1-hydroxybenzotriazole.

In process (a) a suitable protecting group for a hydroxy group is, for example, an arylmethyl group, for example a benzyl group, which may be removed by treatment with an inorganic acid, for example anhydrous hydrogen fluoride, or it may be removed by hydrogenation over a catalyst, for example palladium-on-charcoal; or it may be for example, an esterifying group, for example an acetyl or benzoyl group, which may be removed by hydrolysis with a base, for example sodium hydroxide.

In process (a) a suitable protecting group for a carboxy group is, for example, an esterifying group, for example an arylmethyl group, for example a benzyl group, which may be removed by treatment with an inorganic acid, for example anhydrous hydrogen fluoride, or it may be removed by hydrogenation over a catalyst, for example palladium-on-charcoal; or, for example a tert-butyl group which may be removed by treatment with an organic acid, for example trifluoroacetic acid.

In process (a) particularly suitable protection for a carboxy group at the C-terminus is afforded by the formation of, for example, an ester, for example the ester formed by the coupling of the C-terminus amino acid and a resin, for example a hydroxymethylated styrene-divinylbenzene crosslinked resin; or by the formation of, for example, an amide, for example the amide formed by the coupling of the C-terminus amino acid and a resin, for example a methylbenzhydrylamine styrene-divinylbenzene crosslinked resin.

In process (b) any one of the standard peptide coupling reactions may be used, for example those described in the standard text books on peptide chemistry stated above.

In process (b) it is to be understood that a peptide unit may contain just one protected or unprotected amino acid.

In process (b) a suitable coupling reaction is, for example, a solution-phase coupling reaction, for example an active ester coupling, an azide coupling or a coupling involving N,N'-dicyclohexylcarbodiimide and 1-hydroxybenzotriazole.

In process (b) a suitable reactive derivative of the peptide unit containing a carboxylic acid group, is, for example, an acyl halide, for example an acyl chloride formed by the reaction of the acid and an inorganic acid chloride, for example thionyl chloride; a mixed anhydride, for example an anhydride formed by the reaction of the acid and a haloformate, for example isobutyl chloroformate; or an acyl azide, for example an azide formed by the reaction of the acid and an azide such as diphenylphosphoryl azide.

In process (b) a particularly suitable reactive derivative of the peptide unit containing a carboxylic acid group is, for example, the product of the reaction of the acid and a carbodiimide, for example N,N'-dicyclohexylcarbodiimide or N,N'-diisopropylcarbodiimide, or it is the product of the reaction of the acid, an N-hydroxytriazole, for example 1-hydroxybenzotriazole, and a carbodiimide, for example N,N'-dicyclohexylcarbodiimide or N,N'-diisopropylcarbodiimide.

In process (b) a preferred strategy is, for example, to use a solid-phase synthesis wherein the amino acid which is to become the C-terminus amino acid of a polypeptide of the invention is protected at the alpha amino group and, if necessary, in the side-chain and coupled to a solid support, for example a resin, for example a hydroxymethylated or a methylbenzhydrylamine styrene-divinylbenzene crosslinked resin via an ester or amide linkage respectively, whereafter the protecting group on the alpha-amino group is removed. The amino acid which is to be attached to the C-terminus amino acid is protected at the alpha-amino group and, if necessary, in the side-chain and coupled to the C-terminus amino acid which remains attached to the solid support. The step-wise process of deprotection of the alpha-amino group and coupling to the next amino acid is repeated to give a protected or unprotected polypeptide attached to the solid support.

The protected or unprotected polypeptide may be released from the hydroxymethylated resin solid support by, for example, hydrolysis, for example acid hydrolysis with, for example, an organic acid, for example trifluoroacetic acid or with, for example, an inorganic acid, for example anhydrous hydrogen fluoride or hydrogen bromide; or the polypeptide is released by, for example, alcoholysis, for example methanolysis, in the presence of a base, for example an organic base, for example diisopropylethylamine whereafter, if necessary, the protecting groups are removed using process (a) above.

When a methylbenzhydrylamine resin is used, the protected or unprotected polypeptide may be released from the solid support, for example, by treatment with an inorganic acid, for example hydrogen fluoride, whereafter, if necessary, the protecting groups are removed using process (a) above.

In process (b) a further preferred strategy is, for example, to use a solid-phase synthesis wherein an amino acid which is to become a link within the chain of amino acids forming a polypeptide of the invention is protected at the alpha-amino group and, if necessary, in the side-chain and coupled to a solid support, for example a resin as described above, whereafter the protecting group on the alpha-amino group is removed. The amino acid which is to be attached to the amino acid which has been coupled to the solid support is protected at the alpha-amino group and, if necessary, in the side-chain and coupled to the amino acid which remains coupled to the solid support. The stepwise process of deprotection of the alpha-amino group and coupling to the next amino acid is repeated to give a protected or unprotected polypeptide attached to the solid support.

The protected or unprotected polypeptide may be released from the solid support, for example, using one of the methods described above whereafter a further peptide unit can be coupled using a solution-phase coupling reaction as described for process (b) above, and whereafter, if necessary, the protecting groups are removed using process (a) above.

In process (c) a suitable acylating agent is, for example, an alkanoic acid anhydride, for example a (2–6C)alkanoic acid anhydride or an anhydride derived from a mono-alkyl carbonate, for example from a (4–6C)cycloalkyl carbonate or a (1–4C)alkyl carbonate; or a mixed anhydride, for example an anhydride formed by the reaction of a (2–6C)alkanoic acid, a (4–6C)cycloalkyl carbonate or a (1–4C)alkyl carbonate with a haloformate, for example isobutyl chloroformate.

In process (c) a particularly suitable acylating agent is, for example, an acyl halide, for example a (2–6C)alkanoyl chloride or bromide, a (4–6C)cycloalkoxycarbonyl chloride or bromide or a (1–4C)alkoxycarbonyl chloride or bromide, in the presence of a suitable base, for example an organic base, for example pyridine, 4-dimethylaminopyridine or triethylamine, or an inorganic base, for example potassium carbonate or sodium acetate.

In processes (d) and (e) a suitable reactive derivative of the acid of formula I wherein $R^2$ or Q is hydroxy is, for example, the corresponding acyl halide, for example the acyl chloride formed by the reaction of the acid with an inorganic acid chloride, for example thionyl chloride; the corresponding mixed anhydride, for example the anhydride formed by the reaction of the acid with a haloformate, for example isobutyl chloroformate; or the corresponding ester, for example the ester formed at the end of the step-wise process described above as a preferred strategy for carrying out process (b).

In process (d) suitable esterification conditions are, for example, to react the acid of formula I wherein $R^2$ or Q is hydroxy with a (1–3C)alcohol or a (1–6C)alcohol respectively in the presence of suitable coupling agents, for example a carbodiimide, for example N,N'-dicyclohexylcarbodiimide or N,N'-diisopropylcarbodiimide, and an organic amine, for example a pyridine, for example 4-dimethylaminopyridine.

In process (d) particularly suitable conditions are, for example, to react the reactive derivative of the acid of formula I wherein $R^2$ or Q is hydroxy, comprising the ester formed by the coupling of the acid and the hydroxymethylated resin, with a suitable alcohol, for example a (1–6C)alcohol, in the presence of a suitable base, for example an organic base, for example diisopropylethylamine.

In process (e) particularly suitable conditions are, for example, to react the ester of formula I wherein $R^2$ is (1–3C)alkoxy or Q is (1–6C)alkoxy with ammonia, with a suitable alkylamine, dialkylamine or phenylalkylamine, a suitable cycloalkylamine, N-alkyl-N-cycloalkylamine or dicycloalkylamine, or the appropriate heterocycle in the presence of a diluent or solvent, for example ethanol or tetrahydrofuran.

In process (f) the ester of formula I wherein $R^2$ is (1–3C)alkoxy may be hydrolysed, for example with a base, for example sodium hydroxide in the presence of a diluent or solvent, for example methanol.

In process (g) suitable conditions are, for example, to react the polypeptide having the sequence indicated in formula I wherein $R^1$ is hydrogen or wherein $R^1$ is hydrogen and wherein $R^2$, when Q is $-A^{10}.R^2$, or Q is a hydroxymethylated or methylbenzhydrylamine cross-linked resin, with a suitable (1–6C)aldehyde or (3–6C)ketone each optionally bearing a phenyl substituent, for example, formaldehyde, acetaldehyde, propionaldehyde, butyraldehyde, acetone, benzaldehyde or acetophenone, in the presence of a suitable reducing agent, for example a hydride reducing agent, for example lithium aluminum hydride or diborane in the presence of a diluent or solvent, for example diethyl ether or tetrahydrofuran.

In process (g) a particularly suitable reducing agent is, for example, a hydride reducing agent, for example an alkali metal borohyride or cyanoborohyride, for example sodium borohydride.

When a pharmaceutically-acceptable salt of a polypeptide of formula I is required it may be obtained, for example, by the reaction of a polypeptide of said formula which is sufficiently basic with a suitable acid and by the reaction of a polypeptide of said formula which is sufficiently acidic with a suitable base.

The above processes may be carried out analogously to those described in the accompanying examples. The starting materials for use in the processes of the invention which are not particularly described therein are either known compounds or may be produced and purified by methods well known to one skilled in the art.

As stated above polypeptide compounds of the invention possess bombesin antagonist properties. This activity may be demonstrated, for example, using one or more of the procedures set out below:

(a) An in vitro binding assay which assesses the ability of a test compound to displace radiolabelled gastrin releasing peptide ($[I^{125}]$GRP) from the bombesin receptor of mouse Swiss 3T3 fibroblast cells. The test is similar to that described by I. Zachary and E. Rozengurt, Proc. Nat. Acad. Sci. U.S.A., 1985, 82, 7616, except that the cells are incubated at ambient temperature for 1 hour;

(b) An in vitro assay which assesses the ability of a test compound to inhibit the Neuromedin C stimulated mitogenesis of mouse Swiss 3T3 fibroblast cells as determined by the uptake of $[^3H]$-thymidine. The test is similar to those described by N. Corps., L. Rees and K. Brown, Biochem. Journal, 1985, 231, 781 and I. Zachary and E. Rozengurt, Proc. Nat. Acad. Sci. U.S.A., 1985, 82, 7616, except that GRP (18–27) (0.2 or 0.4 nM) was used to stimulate growth and the test compounds were dissolved in an assay medium containing 0.1% bovine serum albumin and 0.4% dimethylsulphoxide and (c) An in vivo test involving the measurement of the antagonism of the bombesin-induced stimulation of the secretion of the enzyme amylase into the pancreatic duct of the rat by a test compound administered orally, sub-cutaneously or intravenously. Bombesin and the test compound can be administered concomitantly or the test compound can be predosed at any convenient interval, for example 30, 60, 90, 120, 150 or 180 minutes, before bombesin is dosed. Amylase was measured by analysis of the conversion of starch into maltose, on incubation of the starch/amylase mixture at 30° C. for 15 minutes, using a spectrophotometric assay as originally described by P. Bernfield in 'Methods in Enzymology' Vol. I, p17 (Editors Colowick and Kaplan, Academic Press, New York, 1955). Bombesin (5 micrograms/kg, intravenously) causes a large, but submaximal, increase of amylase secretion within 30 minutes.

Although the pharmacological properties of the polypeptide compounds of formula I vary with structural changes, in general polypeptide compounds of formula I possess bombesin antagonist properties at the following concentrations or doses in one or more of the above tests (a) to (c):

Test (a) $IC_{50}$ in the range, for example, 0.1–1000 nM;
Test (b) $IC_{50}$ in the range, for example, 0.1 nM to 5 microM; and Test (c) $IC_{50}$ in the range, for example 20 micrograms/kg to 10 mg/kg intravenously or 20 micrograms/kg to 20 mg/kg sub-cutaneously.

Thus, by way of example, the polypeptide Ac-His-Trp-Ala-Val-D-Ala-His-Leu-NHMe has an $IC_{50}$ of 19.5 nM in test (a); an $IC_{50}$ of 28 nM in test (b); and an $IC_{50}$ of <2 mg/kg sub-cutaneously when dosed 150 minutes before bombesin in test (c); and the polypeptide Ac-His-Trp-Ala-Val-D-Ala-Lys(Z)-Leu-OMe has an $IC_{50}$ of 0.1 nM in test (b); and an $IC_{50}$ of 0.1 mg/kg subcutaneously when dosed 150 minutes before bombesin in test (c).

In general those polypeptide compounds of formula I which are especially preferred have an $IC_{50}$ in the range 0.1 to 100 nM in test (a), an $IC_{50}$ in the range 0.1 to 100 nM in test (b) and an $IC_{50}$ in the range 20 micrograms/kg to 1 mg/kg intravenously in test (c).

No overt toxicity or other untoward effects are present in test (c) when polypeptide compounds of formula I are administered at several multiples of their minimum inhibitory dose.

According to a further feature of the invention there is provided a pharmaceutical composition which comprises a polypeptide of formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients. However, in the case of a composition for oral administration, it may be convenient for the composition to include a coating to protect the polypeptide active ingredient from the actions of enzymes in the stomach.

A composition of the invention may also contain, in addition to the polypeptide of the invention, one or more known antitumour substances selected from, for example, mitotic inhibitors, for example vinblastine; alkylating agents, for example cis-platin, carboplatin and cyclophosphamide; antimetabolites, for example, 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

A preferred composition of the invention is, for example, one suitable for oral administration in unit dosage form, for example a tablet or capsule which contains from 2.5 to 500 mg, and preferably 10 to 100 mg, of polypeptide in each unit dose, or one suitable for parenteral administration which contains from 0.5 to 100 mg of polypeptide per ml, and preferably 1 to 10 mg of polypeptide per ml of solution.

A parenteral composition is preferably a solution in isotonic saline or isotonic dextrose buffered if necessary to a pH of 5 to 9. Alternatively, the parenteral composition may be one designed for slow release in which case the amount of polypeptide per unit dose is in general greater than that required when a conventional injectable formulation is used. A preferred slow release formulation is, for example, a continuous release formulation, for example a formulation of the type described in European Patent Specification No. 58481. A preferred slow release parenteral formulation contains from 10 to 100 mg of polypeptide per unit dose.

The composition of the invention will normally be administered such that a daily oral dose will be from 0.1 mg/kg, to 50 mg/kg and a daily parenteral dose, will be from 20 micrograms/kg to 10 mg/kg.

According to a further feature of the invention there is provided a method for producing a bombesin-antagonist effect in a warm-blooded animal, such as man, in need of such treatment which comprises administering to said animal an effective amount of a polypeptide of formula I or a pharmaceutically-acceptable salt thereof. The invention also provides the use of such a polypeptide of formula I or a pharmaceutically-acceptable salt thereof in the production of a new medicament for use in the treatment of a disease or medical condition mediated by bombesin or a bombesin-like peptide.

A polypeptide of the invention may be used in the treatment, of for example, malignant disease, for example malignant disease in the lung, such as human small cell lung cancer, or for example malignant disease in the pituitary gland, adrenal gland or within the skin. A polypeptide of the invention may also be used in the treatment of conditions associated with the over-production of bombesin or bombesin-like peptides, for example the over-production of gastrin in the gut. The production of gastrin in animals has been linked to the suppression of the release of growth hormone and prolactin. A polypeptide of the invention may therefore be used to promote the availability of growth hormone in man or animals in need of such treatment. A polypeptide of the invention may also be used in the treatment of conditions associated with the failure of normal physiological control of the regulation of gastric acid secretion.

The invention is illustrated, but not limited, by the following Examples in which, unless otherwise stated:

(i) The structures of all polypeptide compounds of the invention were confirmed by mass spectroscopy. Fast-atom bombardment (FAB) mass spectral data were obtained using a VG Analytical MS9 spectrometer and xenon gas. Positive ion data were collected.

(ii) The structures of all polypeptide compounds of the invention were also confirmed by acid hydrolysis and analysis of the resultant amino acids. The hydrolysates were produced by heating each polypeptide or protected polypeptide with 6N hydrochloric acid containing 1% w/v phenol in a sealed evacuated tube at 110° C. for between 16 and 48 hours. The amino acid composition of each hydrolysate was determined with a LKB Model No. 4151 Amino Acid Analyser, and in each case the result was in agreement with the expected composition.

(iii) Crude polypeptide compounds were generally purified by chromatography of a solution of the polypeptide in a 30:70:0.1 v/v mixture of acetonitrile, water and TFA on a preparative reverse-phase column of silica gel (20 mm by 25 cm) using, as eluent at a flow rate of 12–80 ml per minute, a solvent gradient ranging from a 30:70:0.1 v/v to a 70:30:0.1 v/v mixture of acetonitrile, water and TFA. The eluate was monitored continuously by UV absorbance at a value between 230 and 280 nm and the portion of eluate corresponding to the major peak of UV absorbance was collected, evaporated by rotary evaporation in vacuo and the residue was freeze-dried.

(iv) The following abbreviations are used:

DMF = N,N-dimethylformamide,
TFA = trifluoroacetic acid,
DCCI = N,N'-dicyclohexylcarbodiimide,
DICI = N,N'-diisopropylcarbodiimide,
$(Boc)_2O$ = di-tert-butyl dicarbonate,
Boc = tert-butoxycarbonyl
Tos = tosyl (p-tolylsulphonyl)
Z = benzyloxycarbonyl
Ac = acetyl
Bt = 1-benzotriazolyl
Fmoc = fluoren-9-ylmethoxycarbonyl
$OBu^t$ = tert-butoxy
Dt = 3,4-dihydro-4-oxobenzo-1,2,3-triazin-3-yl

EXAMPLE 1

Solid phase synthesis, using an Applied Biosystem 430A peptide synthesiser, of Z-Arg-Pro-Lys(Z)-His-Trp-Ala-Val-D-Ala-His-Leu-OMe.

A hydroxymethylated polystyrene-divinylbenzene resin was used. Boc-Leu-O-[resin] (0.6 g, 0.5 mmole) was placed in the reaction vessel and the following sequence of operations was used to couple Boc-His(-Tos):

| Step | Reagents and Operations | Reaction Time (min) |
|---|---|---|
| 1 | wash with $CH_2Cl_2$ (3 times) | |
| 2 | 2:1 v/v mixture of TFA and $CH_2Cl_2$ | 1.3 |
| 3 | 1:1 v/v mixture of TFA and $CH_2Cl_2$ | 18 |
| 4 | wash with $CH_2Cl_2$ (3 times) | |
| 5 | 1:9 v/v mixture of diisopropylethylamine and DMF (2 times) | 1 |
| 6 | wash with DMF (5 times) | |
| 7 | Boc—His(Tos) anhydride (1 mmol) in DMF | 26 |
| 8 | wash with $CH_2Cl_2$ (5 times) | |

The cycle of steps 1 to 8 was repeated except that in step 7, in place of Boc-His(Tos) anhydride, each of the following reagents was introduced in turn, once per cycle (the reaction times are indicated in parenthesis):

Boc-D-Ala anhydride (16 min), Boc-Val anhydride (26 min), Boc-Ala anhydride (16 min), Boc-Trp anhydride (26 min), Boc-His(Tos) anhydride (26 min), Boc-Lys(Z) anhydride (26 min), Boc-Pro anhydride (26 min) and Z-Arg-OBt tosylate salt (2 mmol, 2 h; then steps 6 and 7 of the cycle are repeated, again with 2 mmol of reagent, to ensure complete coupling).

During the coupling of Z-Arg-OBt 1-hydroxybenzotriazole is released whereupon it cleaves the tosyl protecting groups on the His(Tos) amino acid side chains.

There was thus obtained Z-Arg-Pro-Lys(Z)-His-Trp-Ala-Val-D-Ala-His-Leu-O-[resin] to which methanol (20 ml), DMF (20 ml) diisopropylethylamine (3 ml) were added and the mixture was stirred at ambient temperature for 3 days. The mixture was filtered and the resin was washed with DMF (4×20 ml) and methanol (4×20 ml). The filtrate and washing were combined and evaporated by rotary evaporation in vacuo to give an oil which was freeze-dried. The crude product so obtained was purified by chromatography and freeze-dried. There was thus obtained as a white powder (0.15 g) Z-Arg-Pro-Lys(Z)-His-Trp-Ala-Val-D-Ala-His-Leu-OMe; Mass Spectrum: m/e 1497 (P+1).

The Boc-Leu-O-[resin] used as starting material was obtained from Peninsula Laboratories Europe Ltd.

The Boc protected amino acid anhydrides were prepared in an activator vessel by the reaction of a solution of the appropriate Boc protected amino acid (2 mmol) in $CH_2Cl_2$ with DCCI (1 mmol) at ambient temperature. The mixture was filtered and transferred to a concentrator vessel, the solvent was evaporated, DMF was added and the solution of Boc protected amino acid anhydride was transferred to the reaction vessel at step 7 outlined above.

The Boc protected amino acids, were obtained commercially from Applied Biosystems Ltd. Boc-His(Tos) as its dicylclohexylamine salt was obtained commercially from Applied Biosystems Ltd, the free base being obtained by passing a solution of the salt in $CH_2Cl_2$ through a Biorad AG50-X8 ion exchange column. Boc-Lys(Z) was obtained commercially from Bachem AG.

The Z-Arg-OBt tosylate salt used as starting material was obtained as follows:

A solution of Z-Arg (2 mmol) and p-tolylsulphonic acid (2 mmol), in water was freeze-dried. A mixture of the Z-Arg tosylate salt so obtained, DCCI (2 mmol), 1-hydroxybenzotriazole (2 mmol) and DMF (12 ml) was stirred at ambient temperature in the activator vessel for 40 minutes. The Z-Arg-OBt tosylate salt solution so obtained was transferred to the reaction vessel at step 7 outlined above.

EXAMPLE 2

The process described in Example 1 was repeated using the appropriate C-terminus protected amino acid attached by an ester link to the resin and the appropriate protected amino acid anhydrides or where indicated the appropriate protected amino acid 1-hydroxybenzotriazole ester.

Where appropriate the tosyl protecting group in the side-chain of His(Tos) is removed by treatment of the polypeptide, still attached to the resin, with 1-hydroxybenzotriazole which is either generated in situ from Z-Arg-OBt, Boc-D-Deh-OBt, Boc-D-Gln-OBt, Boc-Asn-OBt or Fmoc-Asp($OBu^t$)-OBt, or it is added as an additional step to steps 1 to 8 outlined in Example 1.

There were thus obtained the polypeptides described in the following table, the structures of which were confirmed by mass spectroscopy and by analysis of their amino acid content after acidic hydrolysis.

TABLE I

| Ex. 2 No. | Polypeptide | Mass m/e (P + 1) |
|---|---|---|
| 1[a] | Z-Arg—Pro—Lys(Z)—His—Trp—Ala—Val—Gly—His—Leu—OMe | 1482.5 |
| 2[a] | Z-Arg—Gly—Lys(Z)—His—Trp—Ala—Val—Gly—His—Leu—OMe | 1442.2 |
| 3[b] | Z-Arg—Pro—Lys(Z)-D-Gln—Trp—Ala—Val-D-Ala—His—Leu—OMe | 1488 |
| 4[c] | Arg—Pro—Lys—His—Trp—Ala—Val-D-Ala—His—Leu—OMe | 1228.6 |
| 5[d,e] | Boc-D-Deh-Pro—Lys(Z)—His—Trp—Ala—Val-D-Ala—His—Leu—OMe | 1532 |
| 6[f,g,h] | Ac-Gly—Asn—His—Trp—Ala—Val—Gly—His—Leu—OMe | 1046 |
| 7[f,g,h] | Ac-Gly—Asn—His—Trp—Ala—Val-D-Ala—His—Leu—OMe | 1060 |

TABLE I-continued

| Ex. 2 No. | Polypeptide | Mass m/e (P + 1) |
|---|---|---|
| 8[d,g,h] | Ac-D-Deh-His—Trp—Ala—Val-D-Ala—His—Leu—OMe | 1115 |
| 9[g,h] | Ac-Lys(Z)—His—Trp—Ala—Val-D-Ala—His—Leu—OMe | 1151 |
| 10[i] | Ac-Lys—His—Trp—Ala—Val-D-Ala—His—Leu—OMe | 1017 |
| 11[h,j] | Ac-D-pcF-His—Trp—Ala—Val-D-Ala-His—Leu—OMe | 1070.5 |
| 12[h,j] | Ac-D-Nal-His—Trp—Ala—Val-D-Ala—His—Leu—OMe | 1086.6 |
| 13[h,j] | Ac-D-Nal-His—Trp—Ala—Val—Gly—His—Leu—OMe | 1072.5 |
| 14[a,k] | Z-Arg—Pro—Lys(Z)—His—Trp—Ala—Val-D-Ala—His—OMe | 1383 |
| 15[h,j,l] | Ac-D-Gln—Trp—Ala—Val-D-Ala—His—Leu—OMe | 880 |
| 16[e,h,j] | Ac-Pro—Lys(Z)—His—Trp—Ala—Val-D-Ala—His—Leu—OMe | 1248 |
| 17[g,h] | Ac-Phe—His—Trp—Ala—Val-D-Ala—His—Leu—OMe | 1036 |
| 18[g,h] | Ac-D-Phe—His—Trp—Ala—Val-D-Ala—His—Leu—OMe | 1036 |
| 19[m] | Boc-D-Arg—His—Trp—Ala—Val-D-Ala—His—Leu—OMe | 1103.6 |
| 20[n,o] | Naphth-2-yloxyacetyl-His—Trp—Ala—Val-D-Ala—His—Leu—OMe | 1031.5 |
| 21[o] | Boc-βAla—His—Trp—Ala—Val-D-Ala—His—Leu—OMe | 1018.1 |
| 22[n,o] | Indol-3-ylacetyl-His—Trp—Ala—Val-D-Ala—His—Leu—OMe | 1004.7 |
| 23[j,p] | Ac-Asp—His—Trp—Ala—Val-D-Ala—His—Leu—OMe | 1004.5 |
| 24[o,q] | Z-D-Glu(OMe)—Trp—Ala—Val-D-Ala—His—Leu—OMe | 987.2 |
| 25[n,o] | 3-Carboxypropionyl-His—Trp—Ala—Val-D-Ala—His—Leu—OMe | 947.9 |
| 26[n,o] | Propionyl-His—Trp—Ala—Val-D-Ala—His—Leu—OMe | 903.4 |
| 27[h,j] | Ac-His—Trp—Ala—Val-D-Ala—His—Leu—OMe | 888.9 |
| 28[r] | βAla—His—Trp—Ala—Val-D-Ala—His—Leu—OMe | 918.6 |
| 29 | D-Glp-Trp—Ala—Val-D-Ala—His—Leu—OMe | 821 |
| 30[h,j,s] | Ac-His—Trp—Ala—Val-D-Ala—His-D-Leu—OMe | 889 |
| 31[h,j] | Ac-D-His—Trp—Ala—Val-D-Ala—His—Leu—OMe | 889 |
| 32[h,j,l] | Ac-D-pcF-D-Gln—Trp—Ala—Val-D-Ala—His—Leu—OMe | 1062 |
| 33[h,j] | Ac-D-pcF-D-pcF-D-His—Trp—Ala—Val-D-Ala—His—Leu—OMe | 1250 |
| 34[h,j] | Ac-Pro—Trp—Ala—Val-D-Ala—His—Leu—OMe | 849 |
| 35[h,j] | Ac-Leu—Trp—Ala—Val-D-Ala—His—Leu—OMe | 865 |
| 36[h,j] | Ac-Pal-Trp—Ala—Val-D-Ala—His—Leu—OMe | 900 |
| 37[n,o] | Propionyl-His—Trp—Ala—Val-D-Ala—His—MeLe-OMe | 917 |
| 38[n,o] | Propionyl-His—Trp—Ala—Val-D-Ala—His—Phe—OMe | 937 |
| 39[n,o] | Propionyl-His—Trp—Ala—Val-D-Ala—Leu—Leu—OMe | 877 |
| 40[n,o] | Propionyl-His—Trp—Ala—Val-D-Ala—Phe—Leu—OMe | 913 |
| 41[n,o] | Propionyl-His(πMe)—Trp—Ala—Val-D-Ala—His—Leu—OMe | 917 |
| 42[n,o] | Propionyl-His(τMe)—Trp—Ala—Val-D-Ala—His—Leu—OMe | 917 |
| 43[n,o] | Propionyl-His—Trp—Ala—Val-D-Ala—Val—Leu—OMe | 865 |
| 44[n,o,t] | Propionyl-His—Trp—Ala—Val-D-Ala-Aib-Leu—OMe | 851 |
| 45[n,o] | Propionyl-His—Trp—Ala—Val-D-Ala—His—OMe | 790 |
| 46[h,j] | Ac-D-pcF-D-His—Trp—Ala—Val-D-Ala—His—Leu—OMe | 1069 |
| 47[h,j] | Ac-Phe—Trp—Ala—Val-D-Ala—His—Leu—OMe | 899 |
| 48[h,j,u] | Ac-D-Pal-Trp—Ala—Val-D-Ala—His—Leu—OMe | 900 |
| 49[h,j] | Ac-D-Leu—Trp—Ala—Val-D-Ala—His—Leu—OMe | 865 |
| 50[h,j,v] | Ac-Lys—Trp—Ala—Val-D-Ala—His—Leu—OMe | 880 |
| 51[h,j] | Ac-His—Trp—Ala—Val-D-Ala—Lys(Z)—Leu—OMe | 1014 |
| 52[h,j] | Ac-His—Trp—Ala—Val-D-Ala—Pro—Leu—OMe | 850 |
| 53[h,j] | Ac-His—Trp—Ala—Val-D-Ala—Thr($CH_2$Ph)—Leu—OMe | 943 |
| 54[w] | Ac-His—Trp—Ala—Val-D-Ala—Thr—Leu—OMe | 853 |
| 55[h,j] | Ac-His—Trp—Ala—Val-D-Ala—Trp—Leu—OMe | 938 |
| 56[h,j] | Ac-His—Trp—Ala—Val-D-Ala—Ser($CH_2$Ph)—Leu—OMe | 930 |
| 57[w] | Ac-His—Trp—Ala—Val-D-Ala—Ser—Leu—OMe | 839 |
| 58[h,j,x] | Ac-His—Trp—Ala—Val-D-Ala—Pal-Leu—OMe | 901 |
| 59[n,o] | Propionyl-His—Trp—Ala—Val-D-Ala—His—Ile—OMe | 903 |
| 60[n,o] | Propionyl-His—Trp—Pro—Val-D-Ala—His—Leu—OMe | 929 |
| 61[n,o] | Propionyl-His—Trp—Leu—Val-D-Ala—His—Leu—OMe | 945 |
| 62[n,o] | Propionyl-His—Trp—Phe—Val-D-Ala—His—Leu—OMe | 979 |
| 63[y] | Propionyl-His—Trp—Ser—Val-D-Ala—His—Leu—OMe | 919 |
| 64[n,o] | Propionyl-His—Trp—Ala—Val-D-Ala—His—Pro—OMe | 887 |
| 65[h,j,z] | Ac-His—Trp—Ala—Val-D-Ala-L-Nal-Leu—OMe | 950 |
| 66[n,o] | Propionyl-His—Trp—Ala—Val-D-Ala—MeLeu—Leu—OMe | 893 |
| 67[n,o] | Propionyl-MeLeu—Trp—Ala—Val-D-Ala—His—Leu—OMe | 893 |
| 68 | Glp-His—Trp—Ala—Val-D-Ala—His—Leu—OMe | 958 |
| 69[h,j] | Ac-His—Trp—Ala—Leu-D-Ala—His—Leu—OMe | 902 |
| 70[h,j] | Ac-His—Trp—Ala—Ile-D-Ala—His—Leu—OMe | 902 |
| 71[aa] | Ac-His—Trp—Ala—Val-D-Ala—Glu—Leu—OMe | 881 |
| 72[bb] | Ac-His—Trp—Ala—Val-D-Ala—Asp—Leu—OMe | 867 |

[a]Z-Arg-OBt tosylate salt (2 mmol × 2) was used rather than the corresponding symmetrical anhydride.

[b]Z-Arg-OBt tosylate salt and Boc-D-Gln-OBt (each 2 mmol × 2) were used rather than the corresponding symmetrical anhydrides.

[c]A mixture of the polypeptide product described in Example 1 (20 mg), palladium-on-charcoal catalyst (5%, 10 mg) and water (5 ml) was stirred at ambient temperature under an atmosphere of hydrogen for 4 hours. The mixture was filtered and the catalyst was washed with water (3 × 5 ml). The combined filtrate and washings were freeze-dried to give the polypeptide product (11 mg) i.e. compound 4 in Table I.

[d]Boc-D-Deh-OBt tosylate salt (2 mmol × 2) was used rather than the corresponding symmetrical anhydride.

[e]The C-terminus amino acids attached to the resin, and the Boc-protected polypeptide resin after the coupling

TABLE I-continued

| Ex. 2 No. | Polypeptide | Mass m/e (P + 1) |
|---|---|---| of each amino acid except after the coupling of the N-terminus amino acid, were treated with a mixture of acetic anhydride (2.5 ml), N-methylmorpholine (0.06 ml), DCCI (0.26 g) and DMF (5 ml) at ambient temperature for 2 hours to ensure that there were no free amino groups capable of causing side reactions.

*f*Boc—Asn-OBt (2 mmol × 2) was used rather than the corresponding symmetrical anhydride. The Boc—Leu—O—[resin] starting material was treated with acetic anhydride as described in footnote e above.

*g*Prior to the removal of the N-terminus Boc-protecting group and to ensure the removal of the tosyl protecting groups in the side chains of all the His(Tos) groups the polypeptide resin was treated with 1-hydroxybenzotriazole (1 mmol) in DMF (20 ml) for 1 hour.

*h*Those polypeptides of the invention having an acyl group at the N-terminus were prepared as follows: the corresponding polypeptide having a Boc group at the N-terminus was synthesised using the procedure of steps 1 to 8 outlined in Example 1. Steps 1 to 6 of the cycle described therein were then repeated to remove the Boc group. A mixture of the polypeptide resin so obtained, DMF (5 ml), N-methylmorpholine (0.06 ml), acetic anhydride (2.5 ml) and DCCI (0.26 g) was stirred at ambient temperature for 2 hours. The N-terminus acetylated polypeptide-resin was isolated and washed in succession with DMF (2 × 10 ml) and methanol (3 × 10 ml). The polypeptide was released from the resin and purified using the procedures described in Example 1.

*i*Compound No. 9 in Example 2 was hydrogenated using the procedure described in footnote c above.

*j*After the acetylation of the N-terminus amino group as described in footnote h above, the polypeptide-resin was treated with 1-hydroxybenzotriazole (1 mmol) in DMF (20 ml) for 1 hour to ensure the removal of the tosyl protecting groups in the side chains of all the His(Tos) groups.

*k*Boc—His(Tos)—O—[resin] used as starting material was obtained from Peninsula Laboratories Europe Ltd.

*l*Boc-D-Gln-OBt (2 mmol × 2) was used rather than the corresponding symmetrical anhydride.

*m*Boc-D-Arg—OBt tosylate salt (2 mmol × 2) was used rather than the corresponding symmetrical anhydride.

*n*Those polypeptides of the invention having a more complex acyl group at the N-terminus (succinic anhydride and propionic anhydride) or they were prepared from the appropriate carboxylic acids (all commercially available) using the procedure described in Example 1 for the preparation of Boc protected amino acid anhydrides from Boc protected amino acids.

*o*Prior to the removal of the Boc protecting group on the N-terminus amino acid to which the appropriate carboxylic acid or amino acid is to be attached, the polypeptide resin was treated with 1-hydroxybenzotriazole (1 mmol) in DHF (20 ml) for 1 hour to ensure the removal of the tosyl protecting groups in the side chains of all the His(Tos) groups.

*p*Fmoc-Asp(OBu$^t$)-OBt (2 mmol × 2) was used rather than the corresponding symmetrical anhydride. The Fmoc protecting group was removed by treating the polypeptide resin so obtained with a 1:5 v/v mixture of piperidine and DMF for 20 minutes. The polypeptide resin was washed with DMF (5 times) and with $CH_2Cl_2$ (3 times). The tert-butyl protecting group was cleaved and the N-terminus acetyl group was introduced using the procedure outlined in footnote h above.

*q*Z-D-Glp anhydride was coupled at the N-terminus. However on release of the polypeptide so formed from the resin using the procedure given in Example 1 ring opening of the Z-D-Glp N-terminus amino acid occurred to form a Z-D-Glu(OMe) N-terminus amino acid.

*r*The Boc protecting group in compound No. 21 in Example 2 was cleaved on treatment with 2M hydrochloric acid in acetic acid (5 ml) for 1 hour at ambient temperature.

*s*Boc-D-Leu—O-[resin] used as a starting material was obtained from Peninsula Laboratories Europe Ltd.

*t*Boc-Aib-ODt (2 mmol × 2) was used in place of the corresponding symmetrical anhydride.

*u*Boc-D-Pal-OBt (2 mmol) was used rather than the corresponding symmetrical anhydride.

*v*The material obtained after the procedures described in the footnotes h and j above had an Ac-Lys(Z)-group at the N-terminus. This was hydrogenated using the procedure described in footnote c above.

*w*This polypeptide was prepared by hydrogenolysis of the benzyl protecting group in the preceding compound using the procedure described in footnote c above.

*x*Boc-Pal-OBt (2 mmol) was used rather than the corresponding symmetrical anhydride.

*y*Fmoc-His(Fmoc)-OBt (2 mmol), Fmoc-Ser(Bu$^t$)-OBt (2 mmol) and Fmoc-Trp-OBt (2 mmol) were used in place of the corresponding Boc protected amino acid anhydrides. resin so obtained with a 1:5 v/v mixture of piperidine and DMF for 20 minutes. The polypeptide resin was washed with DMF (5 times) and with $CH_2Cl_2$ (3 times). The tert-butyl and the propionyl group was introduced using the procedure outlined in footnote n above.

*z*Boc-L-Nal-OBt (2 mmol) was used rather than the corresponding symmetrical anhydride.

*aa*The Boc protecting group was removed from Boc—Leu—O—[resin] and the resin-bound leucine was reacted with Fmoc-Glu(OBu$^t$)-OBt. The Fmoc protecting group was removed using the procedure described in footnote p above. In turn Fmoc-D-Ala-OBt, Fmoc-Val-OBt, Fmoc-Ala-OBt, Fmoc-Trp-OBt and Fmoc-His(Fmoc)-OBt were coupled and the Fmoc and tert-butyl protecting groups cleaved using the procedures described in footnote p above. The acetyl group at the N-terminus was introduced using reaction with acetic anhydride and following the procedure described at the end of footnote h above.

*bb*The procedure described in footnote aa immediately above was repeated except that Fmoc-Asp(OBut)-OBt was used in place of Fmoc-Glu(OBu$^t$)-OBt.

Unless otherwise stated below all of the Boc protected amino acid anhydrides used as starting materials were obtained by the reaction of the corresponding commercially-available Boc protected amino acids as described in the portion of Example 1 concerned with the preparation of starting materials.

Boc-D-Deh-OBt tosylate salt, Boc-D-Gln-OBt, Boc-Asn-OBt, Boc-D-Arg-OBt tosylate salt, Fmoc-Asp(OBu$^t$)-OBt, Fmoc-His(Fmoc)-OBt, Fmoc-Ser(-Bu$^t$)-OBt, Fmoc-Trp-OBt, Fmoc-Glu(OBu$^t$)-OBt, Fmoc-D-Ala-OBt, Fmoc-Val-OBt, Fmoc-Ala-OBt, Boc-Pal-OBt and Boc-L-Nal-OBt were each prepared from the corresponding protected amino acids using the procedure described in that portion of Example 1 concerned with the preparation of starting materials which describes the preparation of Z-Arg-OBt tosylate salt from Z-Arg tosylate salt.

Boc-Aib-ODt was prepared from Boc-Aib-OH using the procedure described in that portion of Example 1 concerned with the preparation of starting materials which describes the preparation of Z-Arg-OBt tosylate salt from Z-Arg tosylate salt except that 3-hydroxy-3,4-dihydrobenzo-1,2,3-triazine was used in place of 1-hydroxybenzotriazole.

Boc-D-Deh was obtained by treatment of the corresponding amino acid with (Boc)$_2$O.

Boc-D-Gln, Boc-Asn, Boc-D-pcF, Boc-$\beta$Ala, Z-D-Glp, Boc-D-Nal and Boc-Aib were obtained from Bachem AG and D-Deh was prepared using the method described in European Patent Specification No. 97031. Boc-Pal was obtained using the procedures described in the International Journal of Peptide and Protein Research, 1984, 24, 197. Fmoc-Asp(OBu$^t$) was obtained from Cambridge Research Biochemicals Ltd.

The Boc-MeLeu-O-[resin] used as a starting material was obtained as follows:

A mixture of a hydroxymethylated polystyrene-divinylbenzene resin (10 g, 4 mmol), Boc-MeLeu (1 g, 4 mmol), DCCI (0.83 g, 4 mmol), 4-dimethylaminopyridine (0.05 g, 0.4 mmol) and methylene chloride (100 ml) was stirred at ambient temperature for 2 days. The mixture was filtered and the resin was similarly treated. The Boc-MeLeu-O-[resin] was filtered off, washed with methylene chloride (3×50 ml), DMF (3×50 ml) and isopropanol (3×50 ml) and dried.

To minimise side reactions the Boc-MeLeu-O-[resin] was acetylated by stirring a mixture of the resin, acetic anhydride (1.1 ml, 0.012 mol), triethylamine (1.7 ml, 0.012 mol) and DMF (50 ml) at ambient temperature for 1 hour. The resin was filtered off and washed with methylene chloride, DMF and isopropanol as above.

The Boc-Phe-O-[resin], Boc-Ile-O-[resin] and Boc-Pro-O-[resin] used as starting materials were obtained commercially.

EXAMPLE 3

Solid phase synthesis, using a Biosearch (SAM 2) peptide synthesiser, of Ac-D-Nal-Pro-D-pcF-His-Trp-Ala-Val-Gly-His-Leu-OMe.

A hydroxymethylated polystyrene-divinylbenzene resin was used. Boc-Leu-O-[resin] (0.6 g, 0.5 mmol) was placed in the reaction vessel and the following sequence of operations was used to couple Boc-His(Tos):

| Step | Reagents and Operations | Reaction Time (min) |
|---|---|---|
| 1 | wash with CH$_2$Cl$_2$ (3 times) | |
| 2 | add a 45:52.5:2.5 v/v mixture of TFA, CH$_2$Cl$_2$ and anisole | 1 |
| 3 | add a 45:52.5:2.5 v/v mixture of TFA, CH$_2$Cl$_2$ and anisole | 20 |
| 4 | wash with CH$_2$Cl$_2$ | |
| 5 | wash with DMF (2 times) | |
| 6 | wash with CH$_2$Cl$_2$ | |
| 7 | add a 1:9 v/v mixture of diisopropylethylamine and CH$_2$Cl$_2$ (3 times) | 0.7 |
| 8 | wash with CH$_2$Cl$_2$ (4 times) | |
| 9 | wash with DMF | |
| 10 | wash with CH$_2$Cl$_2$ | |
| 11 | add Boc—His(Tos) (3.3 mmol) and DICI (3.3 mmol) in DMF | 110 |
| 12 | wash with DMF (2 times) | |
| 13 | wash with CH$_2$Cl$_2$ | |
| 14 | add a 1:9 v/v mixture of diisopropylethylamine and CH$_2$Cl$_2$ | 0.7 |
| 15 | wash with DMF | |
| 16 | add acetic anhydride | 30 |
| 17 | wash with DMF (2 times) | |

The cycle of steps 1 to 17 was repeated except that in step 11, in place of Boc-His(Tos), each of the following reagents was introduced in turn, once per cycle: Boc-Gly, Boc-Val, Boc-Ala, Boc-Trp, Boc-His(Tos), Boc-D-pcF, Boc-Pro and Boc-D-Nal.

The polypeptide so formed, still attached to the resin, was treated with a 1M 1-hydroxybenzotriazole solution in DMF (20 ml) for 1 hour. The resin was washed with DMF (3 times) and CH$_2$Cl$_2$ (3 times). There was thus obtained Boc-D-Nal-Pro-D-pcF-His-Trp-Ala-Val-Gly-His-Leu-O-[resin].

After removal of the Boc group at the N-terminus using steps 1 to 10 above the procedure described in footnote h below Table I in Example 2 was followed to introduce an acetyl group at the N-terminus.

The polypeptide was cleaved from the resin and purified by chromatography using the procedures described in Example 1. There was thus obtained as a white powder (0.05 g) Ac-D-Nal-Pro-D-pcF-His-Trp-Ala-Val-Gly-His-Leu-OMe.

Mass Spectrum: m/e 1350 (P+1).

All of the Boc protected amino-acids were commercially available.

EXAMPLE 4

The process described in Example 3 was repeated using the appropriate C-terminus protected amino acid attached by an ester link to the resin and the appropriate protected amino acid. Those polypeptides, still attached to the resin, which contained a His(Tos) protected amino acid were treated with 1-hydroxybenzotriazole and then with acetic anhydride as described in Example 3. There were thus obtained the polypeptides described in the following table, the structures of which were confirmed by mass spectroscopy and by analysis of their amino acid content after acidic hydrolysis.

TABLE II

| Ex 4 No. | Polypeptide | Mass m/e (P + 1) |
|---|---|---|
| 1 | Ac-D-Nal-Pro-D-pcF-His—Trp—Ala—Val-D-Ala—His—Leu—OMe | 1364.5 |
| 2 | Ac-D-Nal-Pro-D-Nal-His—Trp—Ala—Val-D-Ala—His—Leu—OMe | 1380.5 |
| 3 | Ac-L-Nal-His—Trp—Ala—Val-D-Ala—His—Leu—OMe | 1086.7 |

TABLE II-continued

| Ex 4 No. | Polypeptide | Mass m/e (P + 1) |
|---|---|---|
| 4 | Ac-D-Nal-D-Gln—Trp—Ala—Val-D-Ala—His—Leu—OMe | 1077 |
| 5 | Ac-D-pcF-His—Trp—Ala—Val—Sar—His—Leu—OMe | 1070 |
| 6[a] | Naphth-2-ylacetyl-His—Trp—Ala—Val-D-Ala—His—Leu—OMe | 1015 |
| 7[a] | 4-Chlorophenylacetyl-His—Trp—Ala—Val-D-Ala—His—Leu—OMe | 999 |
| 8[a] | 3-Phenylpropionyl-His—Trp—Ala—Val-D-Ala—His—Leu—OMe | 979 |
| 9 | Ac-D-pcF-His—Trp—MeAla—Val-D-Ala—His—Leu—OMe | 1084 |
| 10 | Ac-D-pcF-His—Trp—Ala—Val-D-Ala—His($\pi$—Me)—Leu—OMe | 1084 |
| 11 | Ac-D-pcF—His—Trp—Ala—Val-D-Ala—His($\tau$13 Me)—Leu—OMe | 1084 |
| 12 | Ac-D-pcF-His—Trp—Ala—MeVal-D-Ala—His—Leu—OMe | 1084 |
| 13 | Ac-His—Trp—Ala—Val-D-pcF-His—Leu—OMe | 999 |
| 14 | Ac-His—Trp—Ala—Val-D-Pro—His—Leu—OMe | 915 |
| 15 | Ac-His—Trp—Ala—Val—Ala—His—Leu—OMe | 889 |
| 16 | Ac-His—Trp—Ala—Val-D-Ser($CH_2$Ph)—His—Leu—OMe | 995 |
| 17[b] | Ac-His—Trp—Ala—Val-D-Ser—His—Leu—OMe | 905 |
| 18[c] | Propionyl-His—Trp—Ala—Val—Sar—His—Leu—OMe | 903 |
| 19[a] | Isobutyryl-His—Trp—Ala—Val-D-Ala—His—Leu—OMe | 917 |
| 20[a] | Isovaleryl-His—Trp—Ala—Val-D-Ala—His—Leu—OMe | 931 |
| 21[a] | Pivaloyl-His—Trp—Ala—Val-D-Ala—His—Leu—OMe | 931 |
| 22[a] | 4-Pyridylacetyl-His—Trp—Ala—Val-D-Ala—His—Leu—OMe | 966 |
| 23[d] | Pr$^i$His—Trp—Ala—Val-D-Ala—His—Leu—OMe | 889 |
| 24[c] | Propionyl-His—Val—Ala—Val-D-Ala—His—Leu—OMe | 816.8 |
| 25[c] | Propionyl-His—Lys(Z(2Cl))—Ala—Val-D-Ala—His—Leu—OMe | 1013.9 |
| 26[e] | Propionyl-His—Lys—Ala—Val-D-Ala—His—Leu—OMe | 845 |
| 27[f] | Propionyl-His—Lys(Ac)—Ala—Val-D-Ala—His—Leu—OMe | 887.8 |
| 28[c,g] | Propionyl-His—Trp—Ala—Val-D-Ala—His—Val—OMe | 889 |
| 29[h] | Ac-His—Trp—Ala—Aib-D-Ala—His—Leu—OMe | 875.4 |
| 30[c] | Propionyl-His—Leu—Ala—Val-D-Ala—His—Leu—OMe | 830 |
| 31[c] | Propionyl-His—Pal—Ala—Val-D-Ala—His—Leu—OMe | 865.7 |
| 32[c] | Propionyl-His—L—Nal—Ala—Val-D-Ala—His—Leu—OMe | 914 |
| 33[c,j] | Propionyl-His—MeTrp—Ala—Val-D-Ala—His—Leu—OMe | 917 |
| 34[j] | Z-His—MeTrp—Ala—Val-D-Ala—His—Leu—OMe | 995 |
| 35[g,k] | Z-His—Trp—Ala—Val-D-Ala—His—Val—OMe | 967.9 |
| 36[l] | Z-His—Trp—Ala—Val-D-Ala—His—MeLeu—OMe | 996 |
| 37 | Ac-His—Trp—Ala—Phe-D-Ala—His—Leu—OMe | 937.6 |
| 38[c] | Propionyl-His-pcF-Ala—Val-D-Ala—His—Leu—OMe | 898 |
| 39 | Ac-His—Trp—Ala—Thr($CH_2$Ph)-D-Ala—His—Leu—OMe | 981 |
| 40[e] | Ac-His—Trp—Ala—Thr-D-Ala—His—Leu—OMe | 891 |
| 41 | Ac-His—Trp—Ala—Lys(Z(2Cl))-D-Ala—His—Leu—OMe | 1086 |
| 42[h] | Ac-His—Trp—Ala—Val—Aib—His—Leu—OMe | 903 |
| 43[c,m] | Propionyl-His—Trp—Ala—Val-D-Ala—His—MeVal—OMe | 903 |
| 44[c,m] | Propionyl-His—Trp—Ala—Val-D-Ala—His—MeAhx-OMe | 917 |
| 45[c] | Propionyl-His—Trp—Ala—Val-D-Ala—His—MeIle-OMe | 917 |
| 46 | Ac-His—Trp—Ala—Val-D-Lys(Z(2Cl))—His—Leu—OMe | 1114 |
| 47[e] | Ac-His—Trp—Ala—Val-D-Lys—His—Leu—OMe | 946.4 |

[a]The polypeptides of the invention having more complex acyl group at the N-terminus were prepared by using the appropriate carboxylic acid in place of an amino acid in the last cycle of the procedure outlined in steps 1 to 17 in Example 3. The appropriate carboxylic acids were all commercially available.

[b]Hydrogenolysis of the benzyl protecting group in Compound No. 16 in Example 4, using the procedure described in footnote c of Example 2, gave this polypeptide.

[c]The polypeptides of the invention having a propionyl group at the N-terminus were prepared by using propionic anhydride in place of acetic anhydride in the procedure described in footnote h below Table I in Example 2.

[d]Those polypeptides of the invention having an N-alkyl substituent at the N-terminus were prepared as follows: The cycle of steps described in Example 3 was repeated using the appropriate C-terminus amino acid attached by an ester link to the resin. After the N-terminus amino acid was coupled steps 1 to 10 of the procedure outlines in Example 3 were completed to remove the N-terminus Boc-protecting group and then the polypeptide resin was treated with 1-hydroxybenzotriazole to remove the tosyl protecting group in the side chain of the His(Tos) group. The polypeptide resin was then suspended in a 100:1 v/v mixture of DMF and acetic acid. Acetone (2.5 equivalents) and sodium cyanoborohydride (2.5 equivalents) were added in turn. The mixture was stirred at ambient temperature for 1 hour and the polypeptide resin was filtered off. The N-alkylated polypeptide was cleaved from the resin using the procedure outlined in Example 3.

[e]This polypeptide was obtained by hydrogenolysis of the preceding compound using the procedure in footnote c of Example 2.

[f]This polypeptide was obtained by acetylation of the preceding compound with acetic anhydride at ambient temperature for 30 minutes.

[g]Boc—Val—O—[resin] was obtained commercially.

[h]Boc—Aib-ODt (2 × 3.3 mmol) was used rather than a mixture of Boc—Aib and DICl and each reaction time was 30 minutes.

[i]Boc—His(Z) was used in place of Boc—His(Tos).

[j]This polypeptide was obtained as a by-product in the preparation of Compound No. 33 in Example 4.

[k]In a repeat preparation of Compound No. 28 in Example 4 Boc—His(Z) was used in place of Boc—His(Tos). Thereby the polypeptide having a Z-group at the N-terminus was obtained as a by-product.

[l]During an attempt to prepare Compound No. 37 in Example 2 by the procedure described in Example 3, Boc—His(Z) was used in place of Boc—His(Tos). Thereby the polypeptide having a Z-group at the N-terminus was obtained as a by-product.

[m]As appropriate, Boc—MeVal—O—[resin] or Boc—MeAhx—O—[resin] were obtained by attaching Boc—MeVal or Boc—MeAhx to the resin using the procedure described at the end of Example 2 for the preparation of Boc—MeLeu—O—[resin].

EXAMPLE 5

A mixture of the polypeptide of the invention described in Example 1 (20 mg) and a 1:2 w/w solution of methylamine in methanol (2 ml) was stirred at ambient temperature for 16 hours. The mixture was evaporated by rotary evaporation in vacuo and the residual oil was freeze-dried. There was thus obtained, as a white powder (20 mg), Z-Arg-Pro-Lys(Z)-His-Trp-Ala-Val-D-Ala-His-Leu-NHMe.

Mass Spectrum: m/e 1495.5 (P+1).

EXAMPLE 6

The process described in Example 5 was repeated using the appropriate polypeptide of the invention, having a methyl ester at its C-terminus end, and the appropriate amine. There were thus obtained the polypeptides described in the following table, the structures of which were confirmed by mass spectroscopy.

TABLE III

| Ex. 6 No. | Polypeptides | Mass m/e (P + 1) |
|---|---|---|
| 1[+] | Z-Arg—Pro—Lys(Z)—His—Trp—Ala—Val-D-Ala—His—Leu—NH$_2$ | 1481.6 |
| 2[+] | Z-Arg—Pro—Lys(Z)—His—Trp—Ala—Val—Gly—His—Leu—NH$_2$ | 1467 |
| 3[*] | Z-Arg—Pro—Lys(Z)—His—Trp—Ala—Val-D-Ala—His—NH(CH$_2$)$_2$CH(CH$_3$)$_2$ | 1438 |
| 4 | Z-Arg—Pro—Lys(Z)-D-Gln—Trp—Ala—Val-D-Ala—His—Leu—NHMe | 1486 |
| 5[+] | Z-Arg—Pro—Lys(Z)-D-Gln—Trp—Ala—Val-D-Ala—His—Leu—NH$_2$ | 1472 |
| 6[a] | Z-Arg—Pro—Lys(Z)-D-Gln—Trp—Ala—Val-D-Ala—His—Leu—NH(CH$_2$)$_2$OH | 1516.71 |
| 7 | Z-Arg—Pro—Lys(Z)-D-Gln—Trp—Ala—Val-D-Ala—His—Leu—N(CH$_3$)$_2$ | 1500.6 |
| 8[b] | Z-Arg—Pro—Lys(Z)-D-Gln—Trp—Ala—Val-D-Ala—His—Leu—NHEt | 1500.5 |
| 9 | Naphth-2-yloxyacetyl-His—Trp—Ala—Val-D-Ala—His—Leu—NHMe | 1030.6 |
| 10 | Indol-3-ylacetyl-His—Trp—Ala—Val-D-Ala—His—Leu—NHMe | 1003.7 |
| 11 | Ac-Asp—His—Trp—Ala—Val-D-Ala—His—Leu—NHMe | 1003 |
| 12 | Ac-His—Trp—Ala—Val-D-Ala—His—Leu—NHMe | 887.9 |
| 13 | Z-Arg—Pro—Lys(Z)—His—Trp—Ala—Val—Gly—His—Leu—NHMe | 481.5 |
| 14 | Propionyl-His—Trp—Ala—Val-D-Ala—His—MeLeu—NHMe | 916 |
| 15[c] | Propionyl-His—Trp—Ala—Val-D-Ala—His—NH-cyclopentyl | 843 |
| 16 | Isobutyryl-His—Trp—Ala—Val-D-Ala—His—Leu—NHMe | 916.6 |
| 17 | Propionyl-His—Trp—Ala—Val-D-Ala—His—Leu—NHMe | 901 |
| 18[c] | Propionyl-His—Trp—Ala—Val-D-Ala—His—NH-cyclohexyl | 857 |
| 19[d,e] | Propionyl-His—Trp—Ala—Val-D-Ala—His—Leu—NHCH$_2$CH$_2$Ph | 992 |
| 20 | Ac-His—Trp—Ala—Val-D-Ala—Lys(Z)—Leu—NHMe | 1013 |
| 21[d,f] | Propionyl-His—Trp—Ala—Val-D-Ala—His-piperidino | 843 |
| 22[d,e] | Ac-His—Trp—Ala—Val-D-Ala—His—Leu—NH-cyclopentyl | 942 |
| 23[d,g] | Ac-His—Trp—Ala—Val-D-Ala—His—Leu-OPr$^i$ | 917 |
| 24[d,g] | Ac-His—Trp—Ala—Val-D-Ala—His—OCH$_2$CH$_2$Pr$^i$ | 832 |

[+] A saturated solution of ammonia in methanol (5 ml) was used
[*] A solution of isopentylamine (0.2 ml) in methanol (5 ml) was used. The mixture was heated to reflux for 6 hours, evaporated by rotary evaporation in vacuo and the residue was purified by chromatography.
[a] The reaction mixture was stirred at ambient temperature for 1 week.
[b] The reaction mixture was stirred at ambient temperature for 2 days.
[c] The appropriate polypeptide methyl ester of the invention was replaced with the corresponding polypeptide resin (0.25 mmol) which was suspended in a 1:1 vv mixture of DMF and methanol (5 ml) each and treated in succession with the appropriate amine (approximately 0.5 mmol) and with potassium cyanide (0.05 g). The mixture was stirred at ambient temperature for 16 hours and filtered. The filtrate was evaporated by rotary evacuation in vacuo and the residual oil was freeze-dried to give the polypeptide of the invention.
[d] As in footnote c above the appropriate polypeptide resin was suspended in a 1:1 v/v mixture of DMF and methanol (5 ml each) and treated in succession with the appropriate amine (approximately 0.5 mol) and with potassium cyanide.
[e] The reaction was carried out at 50° C. for 1 week.
[f] The reaction was carried out at 50° C. for 1 month.
[g] No amine was added and methanol was replaced by the appropriate alcohol. The reaction was carried out at 55° C. for 1 week.

EXAMPLE 7

A mixture of the polypeptide of the invention described in Example 1 (20 mg), a 1N aqueous sodium hydroxide solution (0.03 ml), methanol (1 ml) and water (2 ml) was stirred at ambient temperature for 24 hours. The reaction mixture was chromatographed on a column of Sephadex LH20 using a 1:1 v/v mixture of acetic acid and water as eluent. The fractions containing the product were combined and freeze-dried. There was thus obtained, as a white powder (20 mg), Z-Arg-Pro-Lys(Z)-His-Trp-Ala-Val-D-Ala-His-Leu-OH.

Mass Spectrum: m/e 1482.7 (P+1).

The process described immediately above was repeated except that Compound No. 9 in Example 4 was used as the polypeptide starting material. There was thus obtained Ac-D-pcF-His-Trp-MeAla-Val-D-Ala-His-Leu-OH.

Mass Spectrum: m/e 1070 (P+1).

EXAMPLE 8

Solid phase synthesis, using an Applied Biosystems 430A peptide synthesiser, of Ac-Gly-Asn-His-Trp-Ala-Val-Gly-His-Leu-NH$_2$.

A methylbenzhydrylamine resin was used. Boc-Leu-NH-CH(C$_6$H$_4$.pCH$_3$)-C$_6$H$_4$-[resin] (1 g, 0.5 mmole) was placed in the reaction vessel and the cycle of steps 1 to 8 described in Example 1 was repeated using in turn in step 7 the following reagents (the reaction times are indicated in parentheses):

Boc-His(Tos)anhydride (26 min), Boc-Gly anhydride (16 min), Boc-Val anhydride (1 mmol×2, 26 min), BoC-Ala anhydride (16 min), Boc-Trp anhydride (26 min), Boc-His(Tos) anhydride (26 min), Boc-Asn-OBt (2 mmol×2, 2 h) and Boc-Gly anhydride (16 min).

During the coupling of Boc-Asn-OBt 1-hydroxybenzotriazole is released whereupon it cleaves the tosyl protecting groups on the His(Tos) amino acid side chains. To ensure the complete removal of the tosyl protecting group the Boc-protected polypeptide resin was treated with 1-hydroxybenzotriazole using the procedure described in Example 3.

Steps 1 to 6 of the procedure outlined in Example 1 above were used to remove the N-terminus Boc group. A mixture of the polypeptide-resin so obtained, DMF (5 ml), N-methylmorpholine (0.06 ml), acetic anhydride (2.5 ml) and DCCI (0.26 g) was stirred at ambient temperature for 2 hours. The polypeptide-resin was isolated, washed in succession with DMF (2×10 ml) and methanol (3×10 ml) and dried. There was thus obtained Ac-Gly-Asn-His-Trp-Ala-Val-Gly-His-Leu-NH-CH(C6H4.pCH3)-C6H4-[resin].

A mixture of this polypeptide-resin (1.3 g), freshly distilled hydrogen fluoride (15 ml) and anisole (1.5 ml) was stirred at 0° C. for 1 hour. The solvent was evaporated in vacuo and the residue was washed with diethyl ether (2×15 ml) and extracted with a 1:1 v/v mixture of acetic acid and water (4×10 ml). The extracts were combined, evaporated in vacuo and freeze-dried to give the crude product (0.39 g) which was purified by chromatography on a column of Sephadex G25 eluting with a 1:1 v/v mixture of acetic acid and water. The fractions containing the product were combined, evaporated in vacuo and freeze-dried. The product was further purified by chromatography on a preparative reverse-phase column of silica gel. There was thus obtained, as a white powder (0.2 g), Ac-Gly-Asn-His-Trp-Ala-Val-Gly-His-Leu-NH2.

Mass Spectrum: m/e 1031 (P+1).

The Boc-Leu-NH-CH(C6H4.pCH3)-C6H4-[resin] used as starting material was obtained by coupling Boc-Leu anhydride and methylbenzhydrylamine resin which was obtained from Applied Biosystems Ltd. The coupling reaction was repeated and then the resin was acetylated using the procedure described above.

EXAMPLE 9

The procedures described in Example 8 were repeated using the appropriate Boc-protected amino-acid anhydrides and Boc-His($\pi$-CH2OCH2Ph)-OBt to give Boc-D-Nal-His($\pi$-CH2OCH2Ph)-Trp-Ala-Val-Gly-His($\pi$-CH2OCH2Ph)-Leu-NH-CH(C6H4.pCH3)-C6H4-[resin].

An N-terminus acetyl group was introduced as described in Example 8. The polypeptide was released from the resin and the benzyloxymethyl protecting groups on each His were removed using hydrogen fluoride as described in Example 8. There was thus obtained Ac-D-Nal-His-Trp-Ala-Val-Gly-His-Leu-NH2.

Mass Spectrum: m/e 1057 (P+1).

The Boc-His($\pi$-CH2OCH2Ph)-OBt starting material was prepared from commercially available Boc-His($\pi$-CH2OCH2Ph) using the procedure described in the portion of Example 1 concerned with the preparation of starting materials for the preparation of Z-Arg-OBt tosylate salt from Z-Arg tosylate salt.

What is claimed includes the following:
1. A polypeptide of formula I:

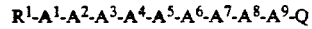

$$R^1\text{-}A^1\text{-}A^2\text{-}A^3\text{-}A^4\text{-}A^5\text{-}A^6\text{-}A^7\text{-}A^8\text{-}A^9\text{-}Q \qquad I$$

wherein $R^1$ is hydrogen or (1-6C)alkyl which may optionally bear a phenyl substituent, and wherein said phenyl substituent may optionally bear a substituent selected from halogeno, (1-4C)alkyl, (1-4C)alkoxy, hydroxy, cyano and nitro, or $R^1$ is (2-6C)alkanoyl which may optionally bear one or more substituents selected from carboxy, (1-4C)alkoxycarbonyl, amino, (1-4C)alkylamino, di[(1-4C)alkyl]amino, phenyl, phenoxy, naphthyl, imidazolyl, naphthyloxy, pyridyl, indolyl and thienyl, and wherein any one or more of said aryl, phenoxy, naphthyloxy or heteroaryl groups may optionally bear one or more substituents selected from halogeno, (1-4C)alkyl, (1-4C)alkoxy, hydroxy, cyano and nitro; or $R^1$ is (4-6C)cycloalkoxycarbonyl; or $R^1$ is (1-4C)alkoxycarbonyl which may optionally bear one or two phenyl substituents and wherein either one or both of said phenyl substituents may optionally bear a halogeno, nitro or (1-4C)alkoxy substituent;

wherein $A^1$ is a direct link to $A^2$, or is Gly, Arg, D-Arg, Lys, Lys(Z), Phe, D-Phe, Asp, L-Nal, D-Nal, D-pcF, D-pfF, D-dcF, Pro, D-Deh, $\beta$Ala or Glp;

wherein $A^2$ is a direct link to $A^3$, or is Gly, Pro or Asn;

wherein $A^3$ is a direct link to $A^4$, or is Lys, Lys(Z), D-Nal or D-pcF;

wherein $A^4$ is His, D-His, MeHis, EtHis, PrHis, His($\tau$-Me), His($\pi$-Me), D-Gln, D-Glu(OMe), D-Glp, Leu, D-Leu, MeLeu, Lys, Pal, D-Pal, Phe, D-Phe, Pro, Arg, Glu, His(COPh), Trp or Thr;

wherein $A^5$ is Trp, MeTrp, Trp(Me), Trp(For), Val, DL-Flg, L-Nal, pcF, Leu, Lys, Pal, Cha, Lys(Z(2Cl)) or Lys(COCH3);

wherein $A^6$ is Ala, MeAla, Aib, Gly, Pro, Leu, Phe, D-Phe, Ser, Val, L-Nal, Thr, Arg or Glu;

wherein $A^7$ is Val, MeVal, Aib, Leu, Ile, Thr(CH2Ph), Thr, Phe, D-Phe, Lys(Z(2Cl)), Ser or DL-Flg;

wherein $A^8$ is Gly, Sar, Ala, D-Ala, D-Ser, D-Ser(CH2Ph), D-pcF, D-Ala(NH2), D-Ala(NHZ(Cl)), Aib, D-Pro, D-Lys, Asp, D-Arg, D-Lys(Z(2Cl)), Val, Ac³c, Ac⁵c or Ac⁶c;

wherein $A^9$ is His, MeHis, His($\tau$-Me), His($\pi$-Me), D-pcF, Aib, Val, Leu, MeLeu, Ala, Ile, Ahx, Ape, Met, Pro, Phe, D-Phe, Gln, Lys, Lys(Z), Pal, Ser, Ser(CH2Ph), Thr, Thr(CH2Ph), Glu, Asp, Asp-(OBu$^t$), Trp or L-Nal; and wherein Q is a group of the formula $-A^{10}.R^2$ in which $A^{10}$ is Leu, D-Leu, MeLeu, Ile, MeIle, Ahx, MeAhx, Aib, Pro, Val, MeVal, Phe, Ape, MeApe, Met, Ser, Gln, Glu or Trp and $R^2$ is hydroxy or amino; or $R^2$ is (1-3C)alkylamino, dialkylamino of up to 4 carbon atoms, or (1-3C)alkoxy, each optionally bearing a hydroxy, (1-3C)alkoxy, amino, (1-6C)alkylamino, dialkylamino of up to 8 carbon atoms, or phenyl-(1-3C)alkylamino substituent, other than in a position alpha to an oxygen or nitrogen atom, or a fluoro-(1-3C)alkyl or phenyl substituent; or $R^2$ is (3-6C)cycloalkylamino, N-alkyl-N-cycloalkylamino of up to 8 carbon atoms, or dicycloalkylamino of up to 12 carbon atoms; or $R^2$ is 1-pyrrolidinyl, piperidino, morpholino, 1-piperazinyl or 4-methylpiperazin-1-yl; or Q is (1-6C)alkoxy, (1-10C)alkylamino or dialkylamino of up to 10 carbon atoms each optionally bearing a hydroxy, amino, (1-3C)alkoxy, (1-6C)alkylamino, dialkylamino of up to 8 carbon atoms, phenyl-(1-3C)alkylamino substituent, other than in a position alpha to an oxygen or nitrogen atom, or a phenyl substituent; or Q is phenyl-(1-3C)alkylamino; or Q is (3-6C)cycloalkylamino, N-alkyl-N-cycloalkylamino of up to 8 carbon atoms or dicycloalkylamino of up to 12 carbon atoms; or Q is 1-azetidinyl, 1-pyrrolidinyl, piperidino, morpholino, 1-piperazinyl or 1-homopiperidinyl each optionally bearing on any available position, including on any available nitrogen atom, a substituent selected from (1-6C)alkyl, phenyl and phenyl-(1-3C)alkyl; and wherein within $R^2$ or Q a phenyl group may optionally bear a substituent selected from halogeno, (1-4C)alkyl, (1-4C)alkoxy, hydroxy and cyano; or a pharmaceutically-acceptable salt of said polypeptide; provided that when -$A^4$-$A^5$-$A^6$-$A^7$-$A^8$-$A^9$-$A^{10}$- is -His-Trp-Ala-Val-Gly-His-Leu-, and -$A^1$-$A^2$-$A^3$- is a direct link, then $R^1$ is not hydrogen or acetyl.

2. A polypeptide of formula I

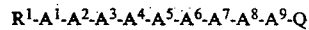    I wherein $R^1$ is hydrogen, methyl, ethyl, propyl, isopropyl, benzyl, acetyl, propionyl, butyryl, isobutyryl, isovaleryl, benzyloxycarbonyl, phenylacetyl, 3-phenylpropionyl, 4-chlorophenylacetyl, 3-chlorophenylacetyl, 4-bromophenylacetyl, 4-fluorophenylacetyl, naphthylacetyl, imidazolylacetyl, pyridylacetyl, thienylacetyl, indolylacetyl, phenoxyacetyl, naphthyloxyacetyl, 3-carboxypropionyl, 3-methoxycarbonylpropionyl, glycyl, 3-aminopropionyl, tert-butoxycarbonyl or cyclopentyloxycarbonyl; wherein $A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

wherein $A^2$ is a direct link to $A^3$, or is Gly, Pro or Asn;

wherein $A^3$ is a direct link to $A^4$, or is Lys, Lys(Z), D-Nal or DpcF;

wherein $A^4$ is His, D-His, MeHis, EtHis, PrHis, His(τ-Me), His(π-Me), D-Gln, Lys, Pal, D-Pal, Phe, Pro, D-Glu(OMe), D-Glp or Trp;

wherein $A^5$ is Trp, MeTrp, Trp(Me), Trp(For), L-Nal, pcF, Lys or Pal;

wherein $A^6$ is Ala, MeAla, Aib, Gly, Leu, Ser, Val or Thr;

wherein $A^7$ is Val, MeVal, Aib, Leu, Ile or Thr;

wherein $A^8$ is Gly, Sar, D-Ala, D-Ser, D-Ser(CH$_2$Ph), D-pcF, Aib or D-Pro;

wherein $A^9$ is His, MeHis, His(τ-Me), His(π-Me), Val, Leu, Pro, Phe, Gln, Lys, Lys(Z) or Pal; and wherein Q is a group of the formula -$A^{10}$.$R^2$ in which $A^{10}$ is Leu, D-Leu, MeLeu, Ile, Ahx, Aib, Val, Phe, Ape or Met and $R^2$ is hydroxy or amino; or $R^2$ is (1-3C)alkylamino, dialkylamino of up to 4 carbon atoms or (1-3C)alkoxy, each optionally bearing an amino, (1-6C)alkylamino or phenyl-(1-3C)alkylamino substituent, other than in a position alpha to an oxygen or nitrogen atom, or a fluoro-(1-3C)alkyl or phenyl substituent; or $R^2$ is (3-6C)cycloalkylamino; or $R^2$ is 1-pyrrolidinyl, piperidino, morpholino or 1-piperazinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is (3-6C)cycloalkylamino;

or Q is 1-pyrrolidinyl, piperidino, morpholino or 1-piperazinyl, each optionally bearing on any available position, including on any available nitrogen atom, a substituent selected from (1-6C)alkyl, phenyl and phenyl-(1-3C)alkyl; and wherein within Q a phenyl group may optionally bear a substituent selected from chloro, methyl, methoxy and hydroxy; or a pharmaceutically-acceptable salt thereof; provided that when -$A^4$-$A^5$-$A^6$-$A^7$-$A^8$-$A^9$-$A^{10}$- is -His-Trp-Ala-Val-Gly-His-Leu-, and -$A^1$-$A^2$-$A^3$- is a direct link, then $R^1$ is not hydrogen or acetyl.

3. A polypeptide of the formula I as claimed in claim 2 wherein $R^1$ is hydrogen, methyl, ethyl, propyl, isopropyl, acetyl, propionyl, isobutyryl, isovaleryl, benzyloxycarbonyl, phenylacetyl, 3-phenylpropionyl, 4-chlorophenylacetyl, naphth-2-ylacetyl, 4-pyridylacetyl, indol-3-ylacetyl, naphth-2-yloxyacetyl, 3-carboxypropionyl or tert-butoxycarbonyl;

$A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

$A^2$ is a direct link to $A^3$, or is Gly, Pro or Asn;

$A^3$ is a direct link to $A^4$, or is Lys, Lys(Z), D-Nal or D-pcF;

$A^4$ is His, D-His, His(τ-Me), His(π-Me), D-Gln, Leu, Lys, Pal, D-Pal, Phe, Pro, D-Glu(OMe) or D-Glp; $A^5$ is Trp or MeTrp; $A^6$ is Ala, MeAla or Aib; $A^7$ is Val; $A^8$ is Gly, Sar, D-Ala, D-Ser, D-Ser(CH$_2$Ph), D-pcF, Aib or D-Pro; $A^9$ is His, MeHis, His(τ-Me), His(π-Me), Leu, Pro, Gln, Phe, Lys, Lys(Z) or Pal; and Q is a group of the formula -$A^{10}$.$R^2$ in which $A^{10}$ is Leu, MeLeu, Phe or Val and $R^2$ is methoxy, amino or methylamino, each optionally bearing a trifluoromethyl or phenyl substituent, or $R^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent;

or $R^2$ is cyclopentylamino or 1-pyrrolidinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is cyclopentylamino, cyclohexylamino, piperidino, 4-phenylpiperidino, morpholino or 4-benzylpiperazin-1-yl;

or a pharmaceutically-acceptable acid-addition salt thereof;

provided that when -$A^4$-$A^5$-$A^6$-$A^7$-$A^8$-$A^9$-$A^{10}$- is -His-Trp-Ala-Val-Gly-His-Leu-, and -$A^1$-$A^2$-$A^3$- is a direct link, then $R^1$ is not hydrogen or acetyl.

4. A polypeptide of formula I

    I wherein $R^1$ is hydrogen, methyl, ethyl, propyl, isopropyl, benzyl, acetyl, propionyl, butyryl, benzyloxycarbonyl, phenylacetyl, 3-phenylpropionyl, 4-chlorophenylacetyl, 3-chlorophenylacetyl, 4-bromophenylacetyl, 4-fluorophenylacetyl, naphthylacetyl, imidazolylacetyl, pyridylacetyl, thienylacetyl, indolylacetyl, phenoxyacetyl, naphthyloxyacetyl, 3-carboxypropionyl, 3-methoxycarbonylpropionyl, glycyl, 3-aminopropionyl, tert-butoxycarbonyl or cyclopentyloxycarbonyl;

wherein $A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

wherein $A^2$ is a direct link to $A^3$, or is Gly, Pro or Asn;

wherein $A^3$ is a direct link to $A^4$, or is Lys, Lys(Z), D-Nal or D-pcF;

wherein $A^4$ is His, D-Gln, Lys, Pal, D-Glu(OMe) or D-Glp;

wherein $A^5$ is Trp, MeTrp, Trp(Me), Trp(For), L-Nal, pcF, Lys or Pal;

wherein $A^6$ is Ala, MeAla, Aib, Gly, Leu, Ser, Val or Thr;

wherein $A^7$ is Val, MeVal, Aib, Leu, Ile or Thr;

wherein $A^8$ is Gly, Sar, Ala, D-Ala, D-Ser, Aib, D-Pro or Phe;

wherein $A^9$ is His, MeHis, His(τ-Me), His(π-Me), Gln or Lys; and wherein Q is a group of the formula -$A^{10}.R^2$ in which $A^{10}$ is Leu, D-Leu, MeLeu, Ile, Ahx, Aib, Val, Ape or Met and $R^2$ is hydroxy or amino; or $R^2$ is (1–3C)alkylamino, dialkylamino of up to 4 carbon atoms or (1–3C)alkoxy, each optionally bearing an amino, (1–6C)alkylamino or phenyl-(1–3C)alkylamino substituent, other than in a position alpha to an oxygen or nitrogen atom, or a fluoro-(1–3C)alkyl or phenyl substituent; or $R^2$ is (3–6C)cycloalkylamino; or $R^2$ is 1-pyrrolidinyl, piperidino, morpholino or 1-piperazinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is (3–6C)cycloalkylamino;

or Q is 1-pyrrolidinyl, piperidino, morpholino or 1-piperazinyl, each optionally bearing on any available position, including on any available nitrogen atom, a substituent selected from (1–6C)alkyl, phenyl and phenyl-(1–3C)alkyl; and wherein within Q a phenyl group may optionally bear a substituent selected from chloro, methyl, methoxy and hydroxy; or a pharmaceutically-acceptable salt thereof;

provided that when -$A^4$-$A^5$-$A^6$-$A^7$-$A^8$-$A^9$-$A^{10}$- is -His-Trp-Ala-Val-Gly-His-Leu-, and -$A^1$-$A^2$-$A^3$- is a direct link, then $R^1$ is not hydrogen or acetyl.

5. A polypeptide of the formula I as claimed in claim 4 wherein $R^1$ is hydrogen, methyl, ethyl, propyl, isopropyl, acetyl, propionyl, benzyloxycarbonyl, phenylacetyl, 3-phenylpropionyl, 4-chlorophenylacetyl, naphth-2-ylacetyl, indol-3-ylacetyl, naphth-2-yloxyacetyl, 3-carboxypropionyl or tert-butoxycarbonyl;

$A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

$A^2$ is a direct link to $A^3$, or is Gly, Pro or Asn;

$A^3$ is a direct link to $A^4$, or is Lys, Lys(Z), D-Nal or D-pcF;

$A^4$ is His, D-Gln, Lys, Pal, D-Glu(OMe) or D-Glp;

$A^5$ is Trp or MeTrp;

$A^6$ is Ala, MeAla or Aib; $A^7$ is Val; $A^8$ is Gly, Sar, D-Ala, Aib or D-Pro; $A^9$ is His, MeHis, His(τ-Me), His(π-Me), Gln or Lys; and Q is a group of the formula -$A^{10}.R^2$ in which $A^{10}$ is Leu or Val and $R^2$ is methoxy, amino or methylamino, each optionally bearing a trifluoromethy or phenyl substituent, or $R^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent;

or $R^2$ is cyclopentylamino or 1-pyrrolidinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is cyclopentylamino, cylcohexylamino, piperidino, 4-phenylpiperidino, morpholino or 4-benzylpiperazin-1-yl;

or a pharmaceutically-acceptable acid-addition salt thereof; provided that when -$A^4$-$A^5$-$A^6$-$A^7$-$A^8$-$A^9$-$A^{10}$- is -His-Trp-Ala-Val-Gly-His-Leu-, and -$A^1$-$A^2$-$A^3$- is a direct link, then $R^1$ is not hydrogen or acetyl.

6. A polypeptide of the formula I as claimed in claim 4 wherein $R^1$ is hydrogen, isopropyl, acetyl, propionyl, benzyloxycarbonyl, 3-phenylpropionyl, 4-chlorophenylacetyl, naphth-2-ylacetyl, indol-3-ylacetyl, naphth-2-yloxyacetyl, 3-carboxypropionyl or tert-butoxycarbonyl;

$A^1$ is a direct link to $A^2$, or is Gly, Arg, D-Arg, Lys, Lys(Z), Phe, D-Phe, Asp, D-pcF, D-Deh, L-Nal, βAla, D-Nal or Pro;

$A^2$ is a direct link to $A^3$, or is Gly, Pro or Asn;

$A^3$ is a direct link to $A^4$, or is Lys, Lys(Z), D-Nal or D-pcF;

$A^4$ is His, D-Gln or D-Glu(OMe);

$A^5$ is Trp; $A^6$ is Ala; $A^7$ is Val;

$A^8$ is Gly, Sar or D-Ala; $A^9$ is His; and

Q is a group of the formula -$A^{10}.R^2$ in which $A^{10}$ is Leu and $R^2$ is methoxy, amino, methylamino, ethylamino or dimethylamino;

or Q is methoxy or isopentylamino;

or a pharmaceutically-acceptable salt thereof; provided that when -$A^4$-$A^5$-$A^6$-$A^7$-$A^8$-$A^9$-$A^{10}$- is -His-Trp-Ala-Val-Gly-His-Leu-, and -$A^1$-$A^2$-$A^3$- is a direct link, then $R^1$ is not hydrogen or acetyl.

7. A polypeptide of formula I $$R^1\text{-}A^1\text{-}A^2\text{-}A^3\text{-}A^4\text{-}A^5\text{-}A^6\text{-}A^7\text{-}A^8\text{-}A^9\text{-}Q \qquad \text{I}$$

wherein $R^1$ is hydrogen, acetyl, propionyl, butyryl, benzyloxycarbonyl, 3-phenylpropionyl, naphthylacetyl, tert-butoxycarbonyl or cyclopentyloxycarbonyl;

wherein $A^1$ is Gly, Arg, Lys(Z), Phe, D-Phe, D-pcF, D-Deh, L-Nal, D-Nal or Pro;

wherein $A^2$ is a direct link to $A^3$, or is Gly, Pro or Asn;

wherein $A^3$ is a direct link to $A^4$, or is Lys, Lys(Z), D-Nal or D-pcF;

wherein $A^4$ is His, D-His or D-Gln;

wherein $A^5$ is Trp; wherein $A^6$ is Ala; wherein $A^7$ is Val;

wherein $A^8$ is Gly or D-Ala; wherein $A^9$ is His;

and wherein Q is a group of the formula $-A^{10}.R^2$ in which $A^{10}$ is Leu and $R^2$ is hydroxy, amino, (1-3C-)alkylamino, dialkylamino of up to 4 carbon atoms or (1-3C)alkoxy;

or Q is (1-6C)alkoxy, (1-6C)alkylamino or dialkylamino of up to 8 carbon atoms;

or a pharmaceutically-acceptable salt thereof.

8. A pharmaceutical composition suitable for producing a bombesin-antagonist effect in a warm-blooded animal in need of such treatment which comprises an effective amount of a polypeptide of formula I as claimed in claim 1, or a pharmaceutically-acceptable salt thereof, in association with a pharmaceutically-acceptable diluent or carrier.

9. A method for producing a bombesin-antagonist effect in a warm-blooded animal in need of such treatment which comprises administering to said animal an effective amount of a polypeptide of formula I as claimed in claim 1 or a pharmaceutically-acceptable salt thereof.

* * * * *